(12) United States Patent
Saxena et al.

(10) Patent No.: US 9,399,123 B2
(45) Date of Patent: *Jul. 26, 2016

(54) SILICONE ADHESIVE COMPOSITIONS

(71) Applicant: Momentive Performance Materials Inc., Albany, NY (US)

(72) Inventors: Anubhav Saxena, Bangalore (IN); Pranav Ramchandra Joshi, Bangalore (IN)

(73) Assignee: Momentive Performance Materials Inc., Waterford, NY (US)

( * ) Notice: Subject to any disclaimer, the term of this patent is extended or adjusted under 35 U.S.C. 154(b) by 42 days.

This patent is subject to a terminal disclaimer.

(21) Appl. No.: 13/722,281

(22) Filed: Dec. 20, 2012

(65) Prior Publication Data

US 2014/0031734 A1    Jan. 30, 2014

Related U.S. Application Data

(60) Provisional application No. 61/582,915, filed on Jan. 4, 2012.

(51) Int. Cl.

| | | |
|---|---|---|
| *C08G 77/26* | (2006.01) | |
| *A61M 35/00* | (2006.01) | |
| *A61K 9/70* | (2006.01) | |
| *C08G 77/38* | (2006.01) | |
| *C08G 77/392* | (2006.01) | |
| *C08G 77/395* | (2006.01) | |
| *C09J 183/06* | (2006.01) | |
| *C09J 183/08* | (2006.01) | |
| *A61F 13/02* | (2006.01) | |
| *C08G 77/22* | (2006.01) | |
| *C08G 77/28* | (2006.01) | |
| *C08G 77/30* | (2006.01) | |
| *C08L 83/08* | (2006.01) | |
| *C08L 83/06* | (2006.01) | |

(52) U.S. Cl.
CPC ............ *A61M 35/00* (2013.01); *A61F 13/0253* (2013.01); *A61K 9/7069* (2013.01); *C08G 77/38* (2013.01); *C08G 77/392* (2013.01); *C08G 77/395* (2013.01); *C09J 183/06* (2013.01); *C09J 183/08* (2013.01); *C08G 77/22* (2013.01); *C08G 77/28* (2013.01); *C08G 77/30* (2013.01); *C08L 83/06* (2013.01); *C08L 83/08* (2013.01)

(58) Field of Classification Search
CPC .... C08G 77/395; C08G 77/392; C08G 77/22; C08G 77/28; C08G 77/30; C08L 83/06; C08L 83/08; C09J 183/06; C09J 183/08
See application file for complete search history.

(56) References Cited

U.S. PATENT DOCUMENTS

| | | | |
|---|---|---|---|
| 2,177,827 A | 10/1939 | Hintze | |
| 2,254,837 A | 9/1941 | Burns | |
| 3,513,183 A * | 5/1970 | Morehouse | 556/428 |
| 3,578,280 A | 5/1971 | Laughlin et al. | |
| 4,768,523 A | 9/1988 | Cahalan et al. | |
| 4,821,828 A | 4/1989 | Schwerzler | |
| 5,232,702 A | 8/1993 | Pfister et al. | |
| 5,380,791 A * | 1/1995 | Panster et al. | 524/837 |
| 5,532,399 A * | 7/1996 | Hager et al. | 556/428 |
| 6,124,490 A | 9/2000 | Gormley et al. | |
| 6,260,373 B1 | 7/2001 | Rockwood | |
| 6,345,512 B1 | 2/2002 | Cosley et al. | |
| 6,461,597 B1 * | 10/2002 | Morita et al. | 424/70.1 |
| 6,747,116 B1 * | 6/2004 | O'Lenick et al. | 528/36 |
| 2007/0107141 A1 * | 5/2007 | Nguyen et al. | 8/405 |
| 2009/0151381 A1 | 6/2009 | Oelmaier et al. | |
| 2010/0272673 A1 | 10/2010 | Horstman et al. | |
| 2014/0134416 A1 * | 5/2014 | Burdinski et al. | 428/219 |

FOREIGN PATENT DOCUMENTS

| | | | |
|---|---|---|---|
| EP | 0312265 A2 | 4/1989 | |
| WO | 2010/095105 A1 | 8/2010 | |
| WO | 2010124187 A2 | 10/2010 | |

OTHER PUBLICATIONS

International Search Report and Written Opinion dated Apr. 26, 2013.
European Search Report dated Dec. 9, 2014.

* cited by examiner

*Primary Examiner* — Margaret Moore
(74) *Attorney, Agent, or Firm* — Joseph S. Ostroff

(57) ABSTRACT

A silicone adhesive composition including an ionic silicone and useful for healthcare applications such as wound care and drug delivery.

46 Claims, 14 Drawing Sheets

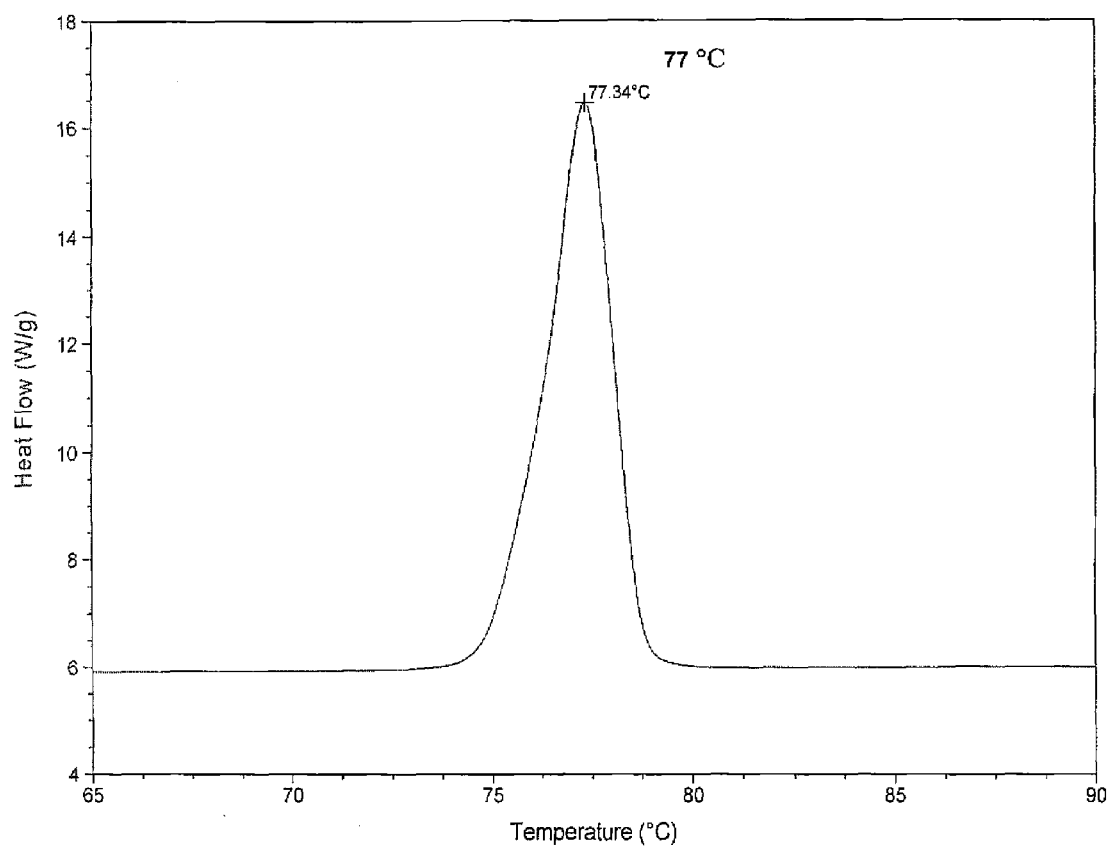
Figure 5(a) DSC thermogram of ibuprofen solid drug

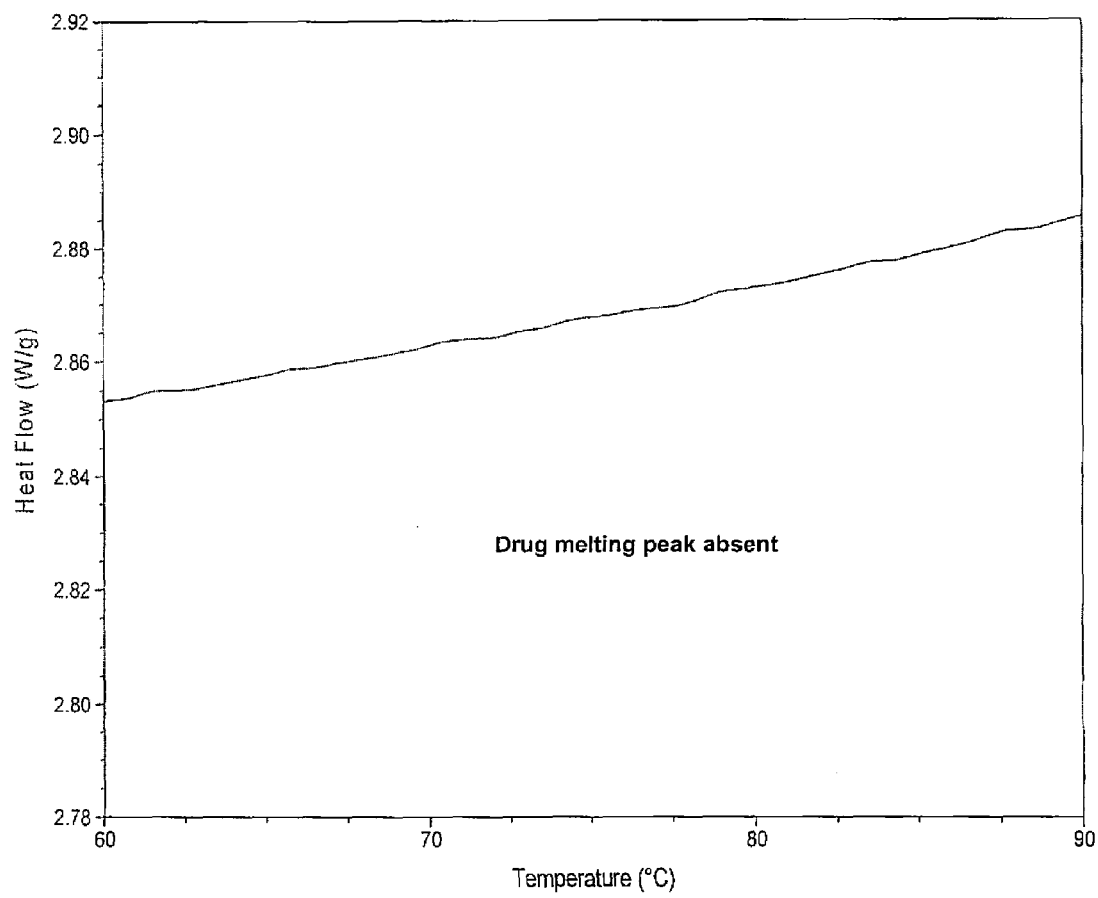
Figure 5(b) DSC thermogram of ibuprofen loaded ionic silicone PSA

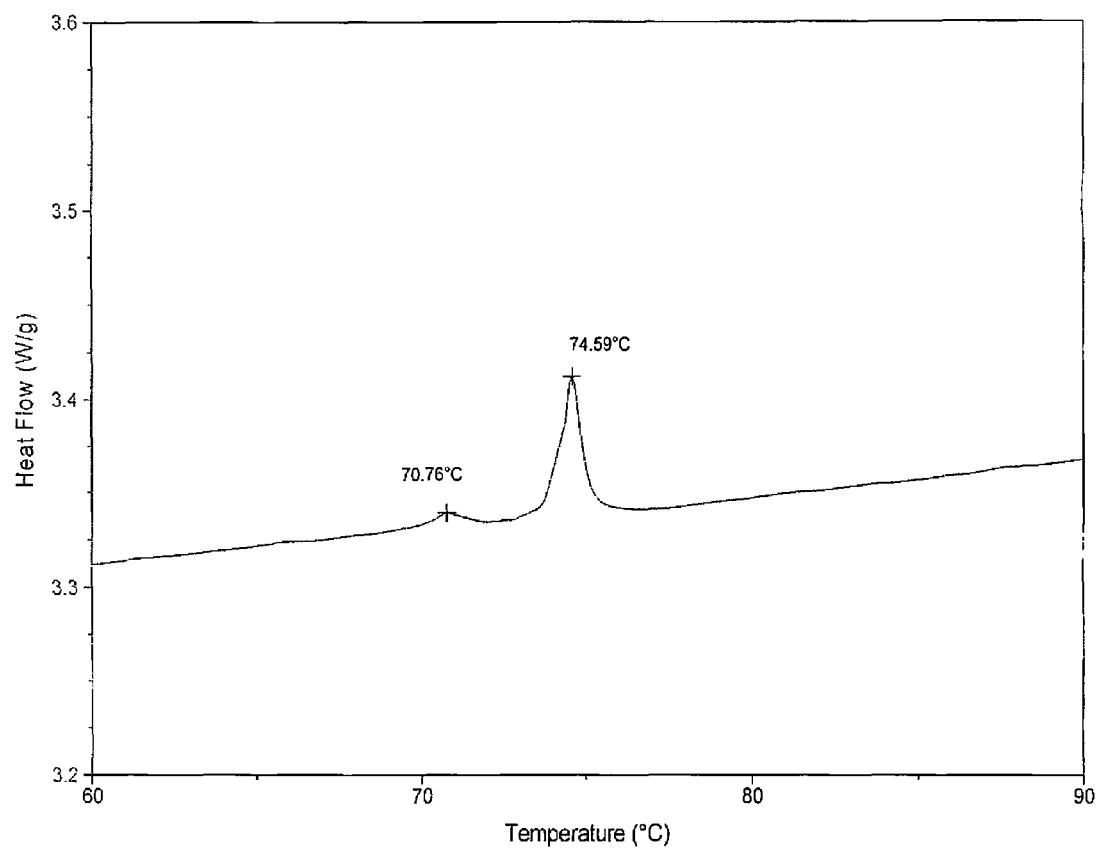
Figure 5(c) DSC thermogram of ibuprofen loaded PDMS film

SILICONE ADHESIVE COMPOSITIONS

CROSS REFERENCE TO RELATED APPLICATIONS

The present application claims priority to U.S. provisional application Ser. No. 61/582,915 filed Jan. 4, 2012, which is herein incorporated by reference.

BACKGROUND

1. Field of the Invention

The present invention relates to adhesives comprising silicone ionomers for numerous applications, particularly for healthcare applications.

2. Background of the Art

The U.S. Pat. No. 5,232,702 describes pressure sensitive silicone adhesive compositions prepared by the addition of a silicate resin to a silicone fluid, along with a cohesive strengthening agent. The cohesive strengthening agent improves adhesive-substrate adhesion and reduces cold flow. Examples of cohesive strengthening agents include nonionic surfactants, fatty acid esters, metallic salts of fatty acids, phosphoric acid, carbonic acid, polysaccharides, carboxypolymethylene, PVP, PVA and precipitated amorphous silica. However, the invention makes no mention of adhesive hydrophilicity.

The European Patent No. 0312265 describes randomly grafted polymers of polyethylene glycol and siloxane, with the polyethylene glycol segment containing a maximum of 15 ethylene oxide units. The silicone adhesive of the present composition involves simple blending of the said polymer with silicone resin, with an optional curing step. The presence of ethylene glycol increased the hydrophilicity and water uptake of the adhesive but compromised its adhesive strength. Increasing the resin content of the adhesive brought back the adhesive strength, but reduced its water uptake. Thus, the hydrophilicity and adhesive nature of the object of this invention were mutually exclusive. Further, there was no mention of increased breathability of the adhesive composition on account of PEG addition.

WO Patent Publication No. 2010124187 describes pressure sensitive adhesives that are silicone-acrylate hybrids, and are prepared by covalent attachment of an acrylate-functional pre-polymer during the condensation crosslinking between silicate resin and gum. Due to the absence of residual acrylate monomers, such a composition is especially useful for skin contact applications. The covalent attachment of the acrylate prepolymer to the silicone adhesive occurs via end-capped alkoxysilane or halosilane groups.

SUMMARY

The present invention describes novel, hydrophilic silicone adhesives that are specifically developed for healthcare applications, specifically in the field of woundcare and drug delivery. Silicone-based adhesives are widely used in woundcare for the attachment of wound dressings, wound drainage pads, ostomy bags, insertion site dressings, to the peri-wound skin and are preferred on account of their biocompatibility and skin-friendly adhesion and debonding properties. Currently used silicone adhesives suffer from a low moisture transport, lack of hydrophilicity and in some cases, a need to be specially formulated for sustained release of antimicrobial or wound healing agents from their matrix. The invention herein is directed to adhesives that are based on silicone ionomers, which are more hydrophilic, have greater moisture permeability and an inherent ability for sustained release of custom antimicrobials. Further, the presence of ionic groups within the adhesive leads to formation of ionic aggregates, which act as fillers that improve the adhesive's mechanical properties and reduce cold flow.

Silicone-adhesive based transdermal patches are commonly used in drug delivery on account of their biocompatibility, skin friendliness, and drug permeability through the patch. However, currently used silicone adhesives for drug delivery suffer from a lack of hydrophilicity and need to be specially formulated for sustained release of therapeutic ingredients from their matrix. The invention describes adhesives that are based on silicone ionomers which are more hydrophilic, on account of the ionic groups. The ionic groups also act as a compatibilizers for certain drugs that are otherwise incompatible with conventional silicones, and affects their release profile, enhancing the delivery of slowly delivered drugs and in some cases, controlling the release of drugs released as a burst from the conventional silicone adhesive matrix.

Furthermore, the presence of co-operative interactions of the ionic groups present in a certain concentration in the ionic silicone allows these materials to self-aggregate to form ionic crosslinking. Additionally, the silicone ionomer possesses reactive functionalities that enable its incorporation in a variety of medical adhesive systems currently in use. The detailed description of the invention is as follows.

BRIEF DESCRIPTION OF THE DRAWINGS

Various embodiments are described below with reference to the drawings wherein:

FIGS. 5(a), 5(b) and 5(c) are a series of graphs illustrating the differential scanning calorimetry of ibuoprofen in the polymer composite silicone adhesive of Example 11;

DETAILED DESCRIPTION OF PREFERRED EMBODIMENT(S)

Figure 1:
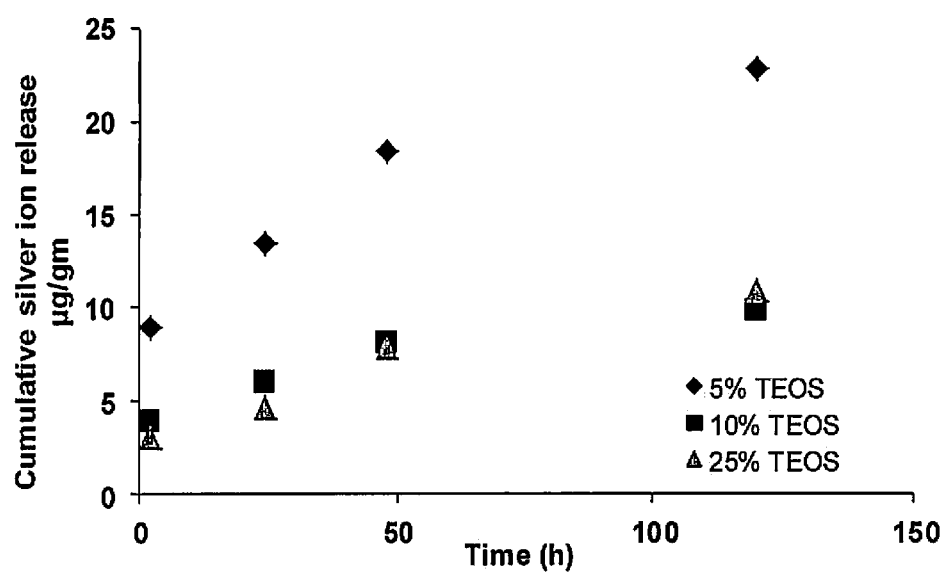
FIG. 1 is a graph illustrating the release of silver ions from the polymer composite silicone adhesive of Example 7.

In the specification and claims herein, the following terms and expressions are to be understood as indicated.

As used in the specification and including the appended claims, the singular forms "a," "an," and "the" include the plural, and reference to a particular numerical value includes at least that particular value, unless the context clearly dictates otherwise.

Ranges can be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

Other than in the working examples or where otherwise indicated, all numbers expressing amounts of materials, reaction conditions, time durations, quantified properties of materials, and so forth, stated in the specification are to be understood as being modified in all instances by the term "about."

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The expression "aliphatic hydrocarbon" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl, and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

It will be understood herein that all measures of viscosity are obtained at 25° C. unless noted otherwise.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

The invention, in its various forms, comprises of the following constituents in suitable combinations, such that the end result has adhesive property. More particularly, the components of the composition of the present invention preferably include one or more of the following: (a) one or more silicone ionomer, (b) one or more silicone compounds as described below, (c) one or more organohydrogen functional silicone compounds as described below, (d) one or more polymer(s), (e) catalyst(s), (f) reaction initiator(s) and (g) additional components as described below.

(a) Silicone Ionomers

In one embodiment, the silicone ionomer component of the present adhesive composition is depicted as below:

$$M^1_a M^2_b M^3_c D^1_d D^2_e D^3_f T^1_g T^2_h T^3_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$ $T^2 = R^{17}SiO_{3/2}$ $T^3 = R^{18}SiO_{3/2}$ $Q = SiO_{4/2}$ where $R^1, R^2, R^3, R^5, R^6, R^8, R^9, R^{10}, R^{11}, R^{13}, R^{15}, R^{16}$ are aliphatic, aromatic or fluoro containing monovalent hydrocarbon radicals containing from 1 to about 60 carbon atoms, specifically from 1 to about 20 carbon atoms and more specifically from 1 to about 8 carbon atoms;

where $R^4, R^{12}, R^{17}$ are monovalent radical bearing ion-pairs and have the formula (II):

$$-A-I^{x-}M_n^{y+}; \qquad (II)$$

where A is a spacing group having at least one spacing atoms selected from a divalent hydrocarbon or hydrocarbonoxy group, where I is an ionic group such as sulfonate $—SO_3^-$, sulfate $—OSO_3^-$, carboxylate $—COO^-$, phosphonate $—PO_3^{2-}$ and phosphate $—OPO_3^{2-}$ group, more specifically sulfonate $—SO_3^-$, where M is hydrogen or a cation independently selected from alkali metals, alkali earth metals, transition metals, metal complexes, quaternary ammonium and phosphonium groups; or, zwitterions having the formula (III):

$$—R'—NR''_2{}^+—R'''—I \qquad (III)$$

where R' is a divalent hydrocarbon radical containing from 1 to about 60 carbon atoms, specifically from 1 to about 20 carbon atoms, and more specifically from 1 to about 8 carbon atoms, where R'' is monovalent hydrocarbon radical containing from 1 to about 60 carbon atoms, specifically from 1 to about 20 carbon atoms and more specifically from 1 to about 8 carbon atoms, and where R''' is divalent hydrocarbon radical containing from 2 to about 20 carbon atoms, specifically from 2 to about 8 carbon atoms and more specifically from 2 to about 4 carbon atoms; and, where I is an ionic group such as sulfonate $—SO_3^-$, sulfate $—OSO_3^-$, carboxylate $—COO^-$, phosphonate $—PO_3^{2-}$ group and phosphate $—OPO_3^{2-}$ group, where $R^7, R^{14}$ and $R^{18}$ are independently selected from hydrogen or monovalent hydrocarbon radicals selected from $—OR^{20}$, unsaturated monovalent radicals, monovalent epoxy group-containing radicals, monovalent sulfur atom-containing radicals, monovalent organosilane groups and monovalent hydroxyl group containing radicals, and a monovalent hydrocarbon group containing one or more of a halogen moiety, a carboxylate moiety, an imine moiety, an isocyanate moiety, an amide moiety, a nitrile moiety, or a tertiary amine moiety containing other than alkyl groups moiety, where $R^{20}$ is hydrogen or a monovalent hydrocarbon radical containing from 2 to about 60 carbon atoms, where superscripts n and y are independently from 1 to 6 and x is a multiple of n and y, where the subscripts a, b, c, d, e, f, g, h, i and j are zero or positive subject to the following limitations: the sum a+b+c+d+e+f+g+h+i+j is greater than or equal to 2 and less than or equal to 6000, specifically a+b+c+d+e+f+g+h+i+j is greater than or equal to 2 and less than or equal to 4000, more specifically a+b+c+d+e+f+g+h+i+j is less than or equal to 2000, and b+e+h is greater than zero.

In yet another embodiment herein, the superscripts are such that a+b≥2, d+e≥0 and g+h≥0 subject to the limitation that b+e+h>0.

In one embodiment herein the monovalent hydrocarbon radicals of $R^1, R^2, R^3, R^5, R^6, R^8, R^9, R^{10}, R^{11}, R^{13}, R^{15}, R^{16}$ are independently selected from the group consisting of methyl, ethyl, n-propyl, iso-propyl, n-butyl, isobutyl, tert-butyl, n-pentyl, iso-pentyl, neopentyl, tert-pentyl, hexyl, such as the n-hexyl group, heptyl, such as the n-heptyl group, octyl, such as the n-octyl and isooctyl groups, 2,2,4-trimethylpentyl, nonyl, such as the n-nonyl group, decyl, such as the n-decyl group, cycloalkyl radicals, such as cyclopentyl, cyclohexyl, cycloheptyl and methylcyclohexyl, and aryl groups such as phenyl, naphthyl; o-, m- and p-tolyl, xylyl, ethylphenyl, and benzyl.

In one other embodiment herein the divalent hydrocarbon group of A in formula (II) is an arylene group selected from the group consisting of $—(CHR')_kC_6H_4(CH_2)_l—, —CH_2CH(R')(CH_2)_kC_6H_4—, —CH_2CH(R')(CH_2)_lC_6H_3R''$ and $—CH_2CH(R')(CH_2)_lC_6H_2R_1R''$ where R' is a hydrogen or defined by $R^1$, R'' is a monovalent radical specifically from about 1 to about 20 carbon atoms, more specifically from about 1 to about 8 carbon atoms, sulfur atom(s), nitrogen atom(s), oxygen atom(s) or a radical containing combinations of the above atoms, where l has a value of 0 to 20, and k has a value of 0 to 20, specifically from 0 to about 10.

In another embodiment, the divalent hydrocarbon group of A in formula (II) is an alkylene group of the formula $—(CHR^{19})_m—$ where m has a value of 1 to 20, specifically, from 1 to about 10 and $R^{19}$ is hydrogen or $R^1$.

In another embodiment the divalent hydrocarbonoxy group of A in formula (II) is selected from $—(CHR^{19})_m—(O—CHR^{19}CH_2)_{m'}—O—(CH_2)_l—$ where l has a value of from 1 to 20, specifically from 1 to about 10, m has a value of 0 to 50 and m' has the value from 0 to 50.

In one other embodiment, in formula (II) M can be a cation independently selected from Li, Na, K, Cs, Ce, Mg, Ca, Ba, Zn, Cu, Fe, Ni, Ga, Al, Mn, Cr, Ag, Au, Pt, Pd, Pb, Sb, Ce, La, Co, Gd, Eu, Ru, Sn and Rh. One skilled in the art can understand that the cations are not limited to the above said, and also can exist in multivalent forms, e.g., $Mn^{2+}$ and $Mn^{3+}$.

In another embodiment in formula (I), $R^7, R^{14}$ and $R^{18}$ are a monovalent hydrocarbon radical selected from the group of the formulae (IV) to (XIV):

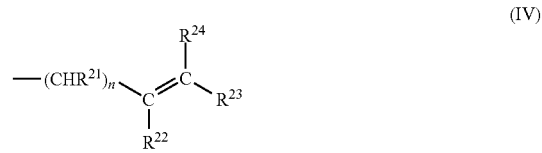

(IV)

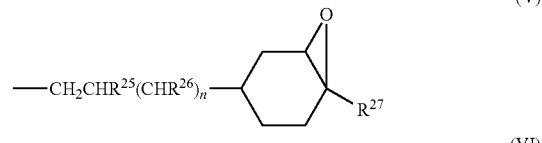

(V)

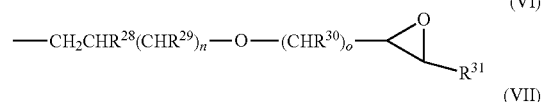

(VI)

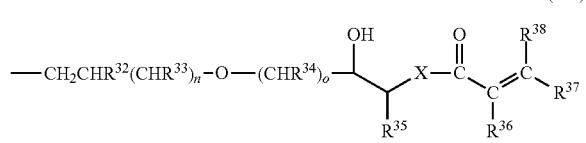

(VII)

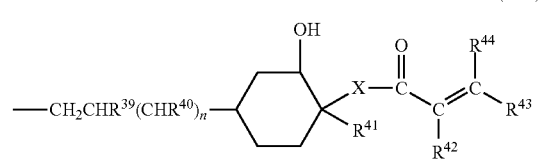

(VIII)

-continued

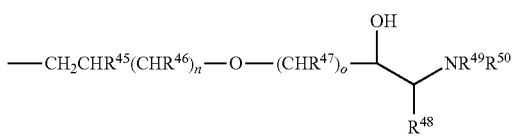
(IX)

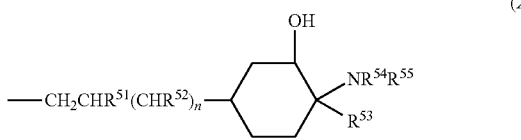
(X)

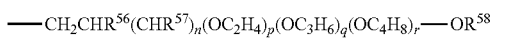
(XI)

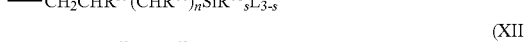
(XII)

(XIII)

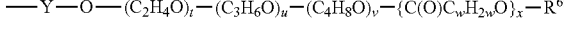
(XIV)

where $R^{21}, R^{26}, R^{29}, R^{30}, R^{33}, R^{34}, R^{40}, R^{46}, R^{47}, R^{52}, R^{63}$ are independently selected from —H, —OH, —$R^{66}$ and aliphatic/aromatic monovalent hydrocarbon having from 1 to about 60 carbon atoms, where $R^{22}, R^{23}, R^{24}, R^{25}, R^{27}, R^{28}, R^{31}, R^{32}, R^{35}, R^{36}, R^{37}, R^{38}, R^{39}, R^{41}, R^{42}, R^{43}, R^{44}, R^{45}, R^{48}, R^{51}, R^{53}, R^{56}, R^{57}, R^{59}, R^{60}, R^{61}, R^{62}$ are independently selected from hydrogen, aliphatic/aromatic monovalent hydrocarbon having from 1 to about 60 carbon atoms, specifically from 1 to about 20 carbon atoms, more specifically from 1 to about 8 carbon atoms, where $R^{58}$ is aliphatic/aromatic monovalent hydrocarbon having from 2 to about 60 carbon atoms, specifically from 2 to about 20 carbon atoms, more specifically from 2 to about 8 carbon atoms, where $R^{49}, R^{50}, R^{54}$ and $R^{55}$ are independently selected from —H, —$C_tH_{2t}$OH and aliphatic/aromatic monovalent hydrocarbon having from 1 to 60 carbon atoms, specifically from 1 to about 20 carbon atoms, more specifically from 1 to about 8 carbon atoms, wherein t is a positive integer, specifically from about 1 to about 20, where L is a monovalent radical independently selected from halogen, $OR^{64}$, —$CO(O)R^{65}$, —N=$CR^{66}_2$, —NCO, —NC(O)$R^{67}$, —C≡N, —N≡N and —$NR^{68}_2$ where $R^{64}, R^{65}, R^{66}, R^{67}$ and $R^{68}$ are independently selected from a group consisting of hydrogen and alkyl, alkenyl, cycloalkyl and aryl containing from 1 to about 60 carbon atoms, specifically from 1 to about 20 carbon atoms, more specifically from 1 to about 8 carbon atoms, where Z is a monovalent radical independently selected from halogen, $OR^{64A}$, —$CO(O)R^{65}$, —N=$CR^{66}_2$, —NCO, —NC(O)$R^{67}$, —C≡N, —N≡N and —$NR^{68A}_2$ where $R^{65}, R^{66}, R^{67}$ are independently selected from a group consisting of hydrogen and alkyl, alkenyl, cycloalkyl and aryl containing from 1 to about 60 carbon atoms, specifically from 1 to about 20 carbon atoms, more specifically from 1 to about 8 carbon atoms, and $R^{64A}$ is hydrogen or selected from a group consisting of alkyl, alkenyl, cycloalkyl and aryl containing from 1 to about 60 carbon atoms, specifically from 1 to about 20 carbon atoms, more specifically from 1 to about 8 carbon atoms, and where $R^{68A}$ is selected from a group consisting of alkenyl, cycloalkyl and aryl containing from 1 to about 60 carbon atoms, specifically from 1 to about 20 carbon atoms, more specifically from 1 to about 8 carbon atoms, where X is divalent radical selected from —O—, —N— and —S— linkages, where Y and B are divalent radical selected from a linear, branched, cyclic hydrocarbon radical or aralkyl radical containing from 1 to about 60 carbon atoms, specifically from 1 to about 20 carbon atoms, more specifically from 1 to about 8 carbon atoms, and may contain heteroatom, where $R^{69}$ is hydrogen or a monovalent alkyl radical with 2 to about 20 carbon atoms or an acyl group, where the subscript n is zero or positive integer and has a value in the range of 0 to about 60, where subscript o is positive integer and has a value in the range of 1 to about 60, where subscripts p, q and r are zero or positive and independently selected from a value in the range of 0 to about 100, subject to the limitation of p+q+r being greater than or equal to 1 and s is zero or positive integer and has a value of 0 to about 2, where t, u, v and x can be zero or positive integers subject to the limitation t+u+v+x is greater than or equal to 1 and w is a positive integer.

(b) Functional Silicone Compound

A silicone compound suitable for use in the composition of the present invention has the formula $A'_aA''_b(OH)_cSiO_{(4-a'-b'-c')/2}$ where A' is an alkenyl group, A" is a group selected from un-substituted or substituted monovalent hydrocarbyl or alkoxy, or cycloepoxy or epoxy, but excluding alkenyl, and a', b', c' are zero or positive numbers such that a'+b'+c'>0.

(c) Organohydrogen Functional Silicone Compound

An organohydrogen functional silicone compound suitable for use in the composition of the present invention is exemplified by the following structure.

where H is a hydrogen atom directly bonded to the silicon atom, A* is a substituted or unsubstituted monovalent hydrocarbyl, hydroxyl or alkoxy, but not alkenyl; d' is a positive number, e' can be 0 or a positive number.

(d) Polymer

The composition of the invention may additionally include a polymer constituent that is capable of non-covalent interactions or covalent bond formation with component (a).

(e) Catalyst

The composition of the invention optionally includes an effective amount of a suitable catalyst to facilitate chemical reaction between components (a), (b), (c) and (d) present in any suitable combination.

(f) Reaction Initiator

The composition of the invention optionally includes an effective amount of reaction initiator to initiate any chemical reactions between components (a) to (d) and optionally catalyzed by component (e).

(g) Additional Components

The composition of the invention preferably includes additional components to add functionality to the adhesive, selected from UV stabilizer, cure initiator, cure inhibitor, cure accelerator, plasticizer, tackifier, pigment, dye, antimicrobial agent, drug, antifungal agent, anti-viral agent, biocide, surfactant, emulsifier, compatibilizer, conductive filler, non-conductive filler, inorganic filler such as calcium carbonate, re-enforcing or non-reinforcing fillers such as finely divided surface treated/untreated metal oxides (e.g. titania, zirconia etc), clay, kaolin, boron nitride, polysaccharides, natural or synthetic fibers, and metal oxide nanoparticles.

Thus, the invention is an adhesive composition resulting from combining some but not all of the components from the list comprising of (a) to (g) and subjecting the same to a suitable thermal treatment or actinic radiation, simultaneously or piece-meal, such that the adhesive finds application in forming a temporary or permanent bond between surfaces of interest.

The components (b) to (g) are described in substantial detail as follows:

(b) Functional Silicone Compound

The silicone polymer component of the present invention is essentially free from any ionic groups and is primarily represented by the following structure:

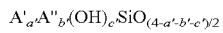

where A' is an alkenyl group, A" is a group selected from un-substituted or substituted monovalent hydrocarbyl, cycloepoxy, epoxy or alkoxy, but excluding alkenyl, and a', b', c' are zero or positive integers such that a'+b'+c'>0.

A' is an alkenyl that is directly bonded to the silicon atom and is exemplified by vinyl, allyl, butenyl, hexenyl and decenyl, but most preferably vinyl.

A" is directly bonded to the silicon atom and is selected from unsubstituted or substituted monovalent hydrocarbyl (excluding alkenyl) epoxy and alkoxy. The hydrocarbyl group can include but is not limited to methyl, ethyl, n-propyl, iso-propyl, n-butyl, isobutyl, tert-butyl, n-pentyl, iso-pentyl, neopentyl and tert-pentyl; hexyl, such as the n-hexyl group; heptyl, such as the n-heptyl group; octyl, such as the n-octyl and isooctyl groups and the 2,2,4-trimethylpentyl group; nonyl, such as the n-nonyl group; decyl, such as the n-decyl group; cycloalkyl radicals, such as cyclopentyl, cyclohexyl and cycloheptyl radicals and methylcyclohexyl radicals. Examples of aryl groups include phenyl, naphthyl; o-, m- and p-tolyl, xylyl, ethylphenyl, and benzyl. Examples of haloalkyl included 3-chloropropyl, 3,3,3-trifluoropropyl, and 2-(nonafluorobutyl)ethyl. Examples of aralkyl groups include ethylbenzyl and 1-phenethyl. The alkoxy can be exemplified by methoxy, ethoxy, n-propoxy, butoxy, acetoxy, and i-propoxy. The epoxy can be linear epoxy or cycloepoxy. OH denotes the hydroxyl group and is directly bonded to the silicon.

(c) Organohydrogen Functional Silicone Compound

The hydride functional siloxane resin is an organohydrogenoligosiloxane or a organohydrogenpolysiloxane of the formula

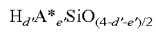

where H is an hydrogen atom directly bonded to the silicon atom, A* is directly bonded to the silicon atom and is a substituted or unsubstituted monovalent hydrocarbyl, hydroxyl, alkenyl or alkoxy; d' and e' are positive integers. The hydrocarbyl group can include but is not limited to methyl, ethyl, n-propyl, iso-propyl, n-butyl, isobutyl, tert-butyl, n-pentyl, iso-pentyl, neopentyl and tert-pentyl; hexyl, such as the n-hexyl group; heptyl, such as the n-heptyl group; octyl, such as the n-octyl and isooctyl groups and the 2,2,4-trimethylpentyl group; nonyl, such as the n-nonyl group; decyl, such as the n-decyl group; cycloalkyl radicals, such as cyclopentyl, cyclohexyl and cycloheptyl radicals and methylcyclohexyl radicals. Examples of aryl groups include phenyl, naphthyl; o-, m- and p-tolyl, xylyl, ethylphenyl, and benzyl. Examples of haloalkyl included 3-chloropropyl, 3,3,3-trifluoropropyl, and 2-(nonafluorobutyl)ethyl. Examples of aralkyl groups include ethylbenzyl and 1-phenethyl. The alkoxy can be exemplified by methoxy, ethoxy, n-propoxy, and i-propoxy.

When the silicone ionomer possesses vinyl or hydride groups, it is required in amounts sufficient to provide an appropriate crosslink density as suitable for the adhesive. When the silicone ionomer or the component (C) as described above possesses epoxy groups, only trace quantities of the organohydrogensiloxane are required as an initiator.

(d) Polymer

The silicone adhesive of the present invention may also be in form of a polymer composite composition, in which case, polymer forms an important component of the composition. The polymers may participate as materials capable of undergoing substantial and relatively rapid crosslinking to form the adhesive composition of the instant invention. The materials undergo such a transformation independently as well as in the presence of components (a) to (c). The crosslinking can be via any of the chemical bond formation mechanisms known to those skilled in the art, and can optionally been initiated thermally or via actinic radiation. In yet another embodiment, the polymers are present in form of their completely or partially polymerized forms such as oligomers and prepolymers. Furthermore, the reactive polymers of the present invention may also participate in additional non-covalent interactions or form covalent bonds with the silicone ionomers. Examples of non-covalent interactions can be due to the compatibility of specific segments of the polymer with the silicone ionomer on account of the following non-limiting attributes: ionic nature, crystallinity, hydrophobicity, polarity, acid-base interactions or hydrogen bonding, or via the formation of co-ordination complexes involving multi-valent functional groups on the silicone ionomer, the reactive polymer, and one or more metal ions in common.

Preferably, the interactions between the silicone ionomer and reactive polymer are ionic interactions between charged groups on the ionomer and on the reactive polymer, whenever such groups are present on the latter.

Even more preferably, the ionically interacting charged groups on the silicone ionomers and the reactive polymer components are the same. Some examples of reactive polymers bearing ionic groups include, but are not limited to: sulfonated poly(styrenes), sulfonated poly(phenylene oxide), 2-acrylamido methyl propanesulfonic acids, sulfoethyl acrylate, sulfopropyl acrylate, and other sulfonated polymer structures for interaction with sulfonated silicones; polymers of (meth)acrylic acid and its derivatives, 2-carboxyethyl acrylate and others that possess pendant carboxyl groups for interaction with carboxyl-modified silicones; phosphoric acid 2-hydroxyethyl methacrylate ester and others that possess phosphate groups for interaction with phosphate-modified silicones, as well as their copolymers and the mixtures of these ionically-modified polymers.

The polymer composite form of the silicone adhesive composition can be obtained by various methods known to those skilled in the art.

In one instance, the polymer composite silicone adhesive can be obtained via the polymerization of the monomers or prepolymers or their mixtures in presence of the ionic silicone.

In another instance, the polymer composite silicone adhesive can be obtained via the polymerization of the functional form of the silicone ionomer in presence of the polymer.

In an even another instance, the polymer composite silicone adhesive is obtainable by the simultaneous or sequential polymerization of the silicone ionomer as well as the monomers or prepolymers or their mixtures.

In yet another instance, the polymer composite silicone adhesive is obtained by the physical or reactive blending of the silicone ionomer and the polymer.

Polymer composite adhesive can also be obtained via covalent bond formation between the silicone ionomers, and the polymer.

In one embodiment, the covalent bonds are formed via condensation reactions between two or more functional groups, with the liberation of a small molecule such as carbon dioxide, methane, water, alcohols, oximes, ketones, bases (e.g. ammonia) and acids (e.g. HCl, $CH_3COOH$).

While it is most preferable that the silicone ionomer and the polymer be largely compatible with one another, the compatibility can also be artificially induced via the use of suitable techniques comprising the use of surfactants, co-surfactants, emulsifiers, solvents, co-solvents and compatibilizers, physical techniques such as use of high shear, rotational motion, turbulence, vibratory motion, heat or cryogenic techniques; use of actinic radiation or suitable combinations thereof as are known to those skilled in the art.

The polymers of the present composition may either be thermoplastics or thermosets. Examples of such crosslinkable, reactive polymers include but are not limited to: ethylenically unsaturated monomers and prepolymers, vinyl functional monomers and prepolymers, hydride functional monomers and prepolymers, hydroxyl functional monomers and polymers, derivatives of (meth)acrylic acid and its esters, polyurethanes, polyethers such as polyethylene oxide, polypropylene oxide, polybutylene oxide, polyphenylene oxide, polyesters, polylactones, polylactides, polyglycolides, polyacids, polyamides, polyethylene, polypropylene, polybutadiene, polybutylene, polyacrylonitrile, polyvinyl chloride, polystyrene, polysulfone, PEEK, polycarbonate, polyepoxides, polyamines, polyanhydrides, polyacids, fluoropolymers such as PTFE, polyvinyldifluoride, synthetic and natural rubber, phenol formaldehyde, melamine formaldehyde, urea formaldehyde, polymers of natural or semi-synthetic origin such as polysaccharides, cellulose, proteins, polypeptides, poly(amino acids) organosilicon polymers such as but not limited to polysiloxanes, polysilicates, polysilanes, polysilsesquioxanes, ionically modified versions of the above, various isomers of the above polymers and various co-polymers in which one or more of the above polymeric entities are present in any known combinations.

In one embodiment, the polymers of the present composition may be present as mixtures of monomers or oligomers that can be cured under certain conditions to form a polymer composite silicone adhesive.

In another embodiment, the polymers are acryl derivatives. Typical acryl derivatives are the condensation products of acrylic acid, alkyl-substituted acrylic acid and various alcohols, amines or similar nucleophilic substituents, and are specifically selected from the group consisting of any monomeric or oligomeric molecule possessing one or more acrylic, methacrylic, ethacrylic groups that can be co-cured with the composition. Preferably, the acrylate derivatives are selected from the group consisting of methacrylate, butylacrylate, propylacrylate, N,N-dimethylacrylamide, methacrylic acid, N-isopropyl acrylamide, 2-hydroxy-ethyl-methacrylate (HEMA), N-vinylpyrrolidone, and methacrylic acid, 3-[tris(trimethylsiloxy)silyl]propyl methacrylate, acrylate and methacrylate functional carbosilane molecules, hexafunctional urethane acrylates, dipentaerythritol pentaacrylate, ethoxylated pentaerythritol tetraacrylate, di-trimethylolpropane tetraacrylate, pentaerythritol triacrylate, trimethylolpropane triacrylate, ethoxylated trimethylolpropane triacrylate, butanediol diacrylate, tripropylene glycol diacrylate, trimethylolpropane trimethacrylate, difunctional oligofunctional urethane acrylates, tetraacrylate monomer, polyester acrylate oligomers, and combinations thereof.

(e) Catalyst

An effective amount of catalyst is included in the adhesive formulation to accelerate the formation of covalent bonds between components (a), (b), (c), or (d) or to polymerize and crosslink component (d). The type of catalyst would depend upon the specific reactive functionalities present on the participating components. As a specific example, when an addition-curable pressure sensitive adhesive is intended, a suitable amount of vinyl functional silicone ionomer (component a) is combined with components b and c. In such a case, curing and adhesive formation occurs via a hydrosilylation reaction between the alkenyl and the hydride groups and is conducted in the presence of any of the known hydrosilylation catalysts preferably at temperatures between about 20 to about 200° C. and about 0.001 to about 100 bars. The reaction is particularly preferred between about 50 to about 150° C., at about 0.1 to about 10 bar, more preferably at normal pressure (1030 mbar). The hydrosilylation catalyst can be exemplified by platinum catalyst such as platinic chloride, chloroplatinic acid, bis(acetylacetonato)platinum, and by platinum group metal catalysts such as palladium and rhodium catalysts. Preferably, the catalyst is platinum, and even more preferably, the platinumt catalyst is present in a soluble complex form. (η5-Cyclopentadienyl)trialkylplatinum complexes, Pt triazenido complex, Pt(AcAc)2, Pt(PPh$_3$)$_2$Cl$_2$ and the type can be used for the photochemically induced addition reaction. Additionally, the catalyst can also be selected from the group consisting of transition metals or transition metal compounds, wherein the transition metal compound are selected from the group consisting of platinum, rhodium, iridium, palladium, nickel and ruthenium, or mixtures thereof.

In another specific embodiment, if the curing reaction takes place between an hydroxyl-functional ionic silicone (a), a hydroxyl function silicate resin (b), the catalyst is a base such as ammonia, potassium hydroxide, alkylamines, metal salts such as tin octanoate, dibutyl tin di-laurate (DBTDL), fatty acid salts of titanium, zirconium, iron and other transition metals.

In yet another specific embodiment, if the adhesive is a copolymer of acrylate functional silicone ionomer (a), it is obtained by free-radical polymerization reaction with other monomers or pre-polymers bearing acrylate functionality. In such case, a catalyst is not strictly necessary, but an initiator is typically required to commence the polymerization reaction.

(f) Initiator

Initiators are typically a part of the adhesive application when components (a) and (c) are the principle participants of the invention. An initiator is also required when the reaction is a UV-initiated hydrosilylation reaction between components (a), (b) and (d). In yet another embodiment, an initiator can be used to facilitate polymerization/crosslinking of component (d). Thus the type of initiator utilized would depend upon the nature of the participating mers and the type of energy source for polymerization. As a specific example, thermal or photo induced crosslinking can be initiated via free radical initiators such as benzoin, benzoin methyl ether, benzoin ethyl ether, benzoin propyl ether, benzion-n-butyl ether, benzoin isobutyl ether, acetoin, butyroin, toluoin, benzil, benzophenone, para methoxybenzophenone, 2,2-diethoxyacetophenone, .alpha.-.alpha.-dimethoxy .alpha.-phenylacetophenone, methylphenyl glyoxylate, ethyphenyl glyoxylate, 4,4'-bis-(dimethylaminobenzophenone), propiophenone, acetophenone, 1-hydroxycyclohexyl phenyl ketone, 2,2-diethoxyacetophenone, ethlphenylpyloxylate, phenanthraquinone, and 2-hydroxy-2-methyl-1-phenyl-propan-1-one; sulfur compounds such as tetramethylthiuram monosulfide and tetramethylthiuram disulfide; azo compounds such as azobisisobutyronitrile and azobis-2,4-dimethylvaleronitrile; and peroxide compounds such as benzoyl peroxide, dicumyl peroxide, acetone peroxide, methyl ethyl ketone peroxide, and di-tert-butyl peroxide, thioxanthone photoinitiators like 7-chlorothioxanthone, 2,4-diethylthioxanthone and 2,4-diisopropylthioxanthone and acylophosphine oxide photoinitiators. The initiators can also comprise of commercially available formulations with proprietary composition, as exemplified by the Irgacure family (Ciba Specialty Chemicals) and VAZO series (DuPont).

In another specific embodiment of the invention, the adhesive can comprise components with UV-cured epoxy functionalities. In such an embodiment, the adhesive of the present invention preferably contain 0.1-20 parts by weight of a cationic photoinitiators particularly those known in the prior arts such as diaryliodonium salts, triarylsulfonium salts, triarylselenonium salts, tetraarylphosphonium salts and aryldiazonium salts, represented by the formulas $R^{29}_2I^+Y^-$, $R^{29}_3S^+Y^-$, $R^{29}_3Se^+Y^-$, $R^{29}_4P^+Y^-$ and $R^{29}N_4^+Y^-$ respectively (wherein, $R^{29}$ represents an aryl group, and $Y^-$ represents an anion such as $SbF_6^-$, $AsF_6^-$, $PF_6^-$, $BF_4^-$, $HSO_4^-$ and $ClO_4^-$.

(g) Additional Components

In addition, these other components can be present as additives to further enhance the performance of the adhesive and may include pigments, colorants, mold release agents, plasticizers, tackifiers, UV absorbers, antioxidants, as well as various active agents of value that can be retained within the cured polymer matrix or released at a controlled rate to deliver a desired effect. In a healthcare-related application, examples of such active agents include drugs, skin permeation enhancers, anti-inflammatory agents, antimicrobial agents, biocides, pain relievers, analgesics, anti-allergens, antibiotics, blood pressure regulators, anti-pyrogens, hormones and hormone analogs, enzymes, proteins and peptides, antifungal agents, antibacterial agents, antiviral agents, and combinations thereof. The functional additives may be dissolved or dispersed in the final composition. In one embodiment of the invention, the functional additives are present in ionic form which can be bound to the ionic moieties present on the silicone ionomers or on the polymer, and are released in a sustained manner through an ion-exchange mechanism with the surrounding environment. Examples of such additives include the broad spectrum antimicrobial basic compound chlorhexidine, ionic copper, and ionic silver.

Additionally, the mechanical, thermal properties and electrical properties of the final cured compositions may further be improved by the incorporation of fillers within the matrix. The fillers can be present at a loading of 0% to 90% of the total weight of the final composition. Preferably, the fillers are present at a loading of 1% to 50% of the total weight of the composition. Examples of suitable filler materials include but are not limited to: silicone resins, silica, nanosilica, fumed silica, particulate forms of oxides of titanium, cerium, aluminum, zirconium and other metals and metalloids present with or without surface modification; carbon black, carbon nanotubes, graphite, graphene, glass fibers, inorganic fillers such as talc, carborundum, mica, boron nitride, inorganic fillers such as clay, kaolin, calcium carbonate, fillers of biological origin such as polysaccharides, and suitable combinations thereof.

Adhesive Composition

The silicone adhesive composition of the present invention can be formulated using a combination of some or all of the components (a) to (h) described above using suitable techniques of a chemical or physical nature.

In one specific embodiment, the adhesive is a silicone pressure sensitive adhesive comprising of polymer networks prepared specifically by conducting a hydrosilylation reaction between one or more vinyl functional silicone ionomers, one or more vinyl-terminated siloxane resins, and one or more hydride-functional polydiorganosiloxane crosslinker bearing at least two hydrogen atoms per molecule, and in the presence of suitable transition metal-based catalyst as described. The adhesive and cohesive properties of the silicone network can be optimized by adjusting the density of crosslinking, via the ratio of silicon bonded hydride groups to silicon bonded alkenyl groups.

In yet another specific embodiment, the adhesive is a polymer composite composition between the silicone ionomer and a three-dimensional polysilicate of tetraethyl orthosilicate (TEOS) prepared by condensation of TEOS in presence of a tin-based catalyst.

In a further specific embodiment, the silicone adhesive is in form of a polymer emulsion, which yields an adhesive layer upon application to a suitable substrate and subsequent evaporation of the aqueous phase.

Some non-limiting types of silicone adhesives that are the object of the present invention and their participating components (from the list comprising of (a) to (g)) is as follows, with component (g) being optional in each case:

i. Addition cure adhesive:
1. Vinyl (a), (b), (c), (e), optionally (f)
2. Epoxy (a), Epoxy (b), (e), Si—H (f)
ii. Condensation cure adhesive: hydroxy or alkoxy (a), (b), (e)
iii. Copolymer adhesive: (a), (d), (f)

Industrial Applicability:

The silicone adhesives comprising the present invention have wide applicability specifically in the healthcare field due to desirable properties of the siloxanes such as customizable tack, atraumaticity (pain-free removal), controlled release of actives, breathability and biocompatibility.

In wound care, the adhesive compositions can be utilized in wound dressings, as an adhesive to affix wound dressings, ostomy bags, dressings for catheter insertion wounds, surgical wounds, surgical closure sites where closure is done by staples or sutures, antimicrobial barrier and attachment of medical electrodes, sensors as well as waste collection devices to the skin.

A particularly useful healthcare related application that can comprise the present invention is skin patches for transdermal drug delivery. Such systems are known in current art, and provide the combined advantages of acrylic and silicone adhesive systems. However, incorporation of acrylate functional silicone ionomers in the system will enable compatibility with numerous hydrophilic drugs while increasing the breathability of the system over and above that provided by the organic monomers alone.

The aforementioned transdermal delivery system is typically formulated as a drug-in-adhesive matrix or its different variants, and comprise of one or more agents of therapeutic value. Additionally, many such agents can be associated with the ionic moieties within the silicones, which may further reduce their potential to re-crystallize, thereby increasing the shelf life.

Silicone-based pressure sensitive adhesives with drugs dissolved or dispersed in the polymer matrix are commonly used devices for transdermal delivery. However, on account of their hydrophobicity and inertness, many hydrophilic drugs are unable to interact with the silicones, and as a result, crystallize in the patch. Due to the ionic nature of silicones used in the present invention, such drugs are better able to interact with the silicones, leading to a modified and desirable release profile.

Additionally, the water absorbing capability of silicone ionomers implies that a greater portion of the drug is accessible to the body fluids, which translates into a better economic value for the end-user and is also safe for disposal, from a regulatory standpoint.

Apart from the above description, the composition forming the subject of present invention can be manifested in various physical forms incorporating numerous substances of therapeutic value, and depending upon the intended application. Examples of pharmaceutically active ingredients that can included in the healthcare compositions comprising radiation crosslinked silicone ionomers include but are not limited to: bioactives, anti-acne agents, anti-ageing agents, anti-fungal agents, anti-caries agents, anti-fungal agents, anti-microbial agents, anti-oxidants, anti-cancer, anti-viral, anti-inflammatory, anti-coagulants, hemostatic agents, blood pressure regulators, exfoliants, hormones and hormone analogs, enzymes, medicinal compounds, biocides, external analgesics, oral care drugs, oxidizers, reducing agents, skin protectants, essential oils, insect repellants, UV absorbers, sun protection agents, pigments, hydrating agents, vitamins and combinations thereof.

The term drug as used herein is used to include substances defined as drugs under the Federal Food, Drug and Cosmetic Act, Pub L. No. 75-717, 52 STAT 1040 (1938), 21 U.S.C. Sev. 201 and generally are substances intended for use in the diagnosis, cure, mitigation, treatment or prevention of disease in man or other animals, and substances, other than food, intended to affect the structure or any function of the body of man or other animal. Some representative examples of such substances are drugs that act upon the central nervous system such as clozapine, risperidone, chordiazepoxide, buspirone, desipramine, maprotiline, timolol, selegiline; drugs affecting renal and cardiovascular function such as acetazolamide, isosorbide, furosemide, chlorothiazide, amiloride, captopril, enalapril, lisinopril, nifedipine, verapamil, lidocaine, propranolol, amiodarone, pravastatin, probucol, oxycontin; drugs affecting gastrointestinal function such as cimetidine, omeprazole and ranitidine; drugs for treatment of helminthiasis such as thiabendazole and mebendazole; drugs for the treatment of microbial diseases such as trimethoprim, norfloxacin, ciprofloxacin, penicillin, kanamycin, fluconazole, acyclovir, ritonavir, and ganciclovir; drugs for the treatment of neoplastic diseases such as dacarbazine, busulfan, and triazenes; drugs for treatment of nutrient deficiency such as folic acid, niacinamide, ascorbic acid and thiamine; drugs for hormonal replacement therapy such as testosterone and other androgenic steroids, progestational drugs, estradiol and their analogues and norethindrone; drugs for inhibition of adrenocortical hormones such as cortisol, cortisone and prednisone; drugs used in dermatology such as betamethasone, dipropionate, hydrocortisone, dexamethasone sodium phosphate, retinal, tretinoin, isotretinoin, dapsone, calipotriene, ketoconazole, clotrimazole itraconazole and arotinoid; anti-inflammatory agents such as ibuprofen, ketoprofen, diclofenac; anti-histamines such as azelastine, hydroxyzine, desloratadine, carbinoxamine, fexofenadine and brompheniramine; respiratory agents such as tadalafil, laronidase, ciclesonide and indacaterol maleate; sympathomimetics such as catecholamines, epinephrine and dopamine; miotics; cholinergic agonists such as alvameline, muscarine, nicotine and pilocarpine; humoral agents; anti-spasmodics such as baclofen, tizanidine and dantrolene; anti-depressant drugs; anti-diabetic drugs; anti-anorectic drugs; tranquilizers; antipsychotics such as olanzapine, risperidone, quetiapine, ziprasidone and amisulpride; anti-pyretics such as paracetamol, nabumetone; drugs for Parkinson's disease, anti-malarials, anti-ulcerative agents, therapeutic agents and combinations thereof.

The active agents may be dissolved or dispersed in the final composition. In one embodiment of the present invention, the functional additives are present in ionic form which can be bound to the ionic moieties present on the silicone ionomers or the polymer, and are released in a sustained manner through an ion-exchange mechanism with the surrounding environment.

In addition to above, various excipients can be used in the present adhesive composition. The term excipient is defined herein as additive used to convert pharmacologically active compounds into pharmaceutical dosage forms. Representative, non-limiting examples of such additives include sugars and sugar derivatives such as acacia, dextrin, dextrose, fructose, lactose, maltodextrin, mannitol, sorbitol, sucrose and xylitol; starch and derivatives; cellulosic materials such as sodium carboxymethylcellulose, microcrystalline cellulose, cellulose acetate phthalate, sodium croscarmellose, methyl cellulose, ethyl cellulose, HPMC, hydroxypropyl cellulose; polysaccharides such as xanthan gum, guar gum; polyethers such as poloxamers, and polyoxyalkylene ethers; polyvinyl alcohols and acetates; acrylic acid and methacrylic acid polymers such as Carbopol, Carbomer, Covacryl, polacrilin potassium; pyrrolidone derivatives such as povidone, crosspovidone and Kollidon; glycouran polymers such as hyaluronic acid, alginic acid, alginate, agar; and other excipients such as cholesterol, lecithin, gelatin and mallic acid.

In some cases, the active agent to be delivered does not have the adequate properties to freely diffuse into the skin to allow attainment of appreciable plasma levels of the active agent. In some other cases, the skin of a patient may have higher barrier properties that prevent drug diffusion in significant amounts. In such a situation, certain substances known as skin permeation enhancers can be a part of adhesive composition, which increase the permeability of the active agents loaded in the adhesive.

Examples of permeation enhancers include but are not limited to solvents such as diemthyl sulfoxide, dimethyl acetamide, dimethyl formamide, propylene glycol, ethylene glycol, tetraethylene glycol; azone; pyrrolidones; fatty acids such as oleic acid, linoleic acid, lauric acid, myristic acid and capric acid; terpenes and terpenoids; menthol; oxazolidinones such as 4-decyloxazolidin-2-one and urea.

Probable Methods of Use

The silicone adhesives of the present invention, along with the various active agents and other additives, can be utilized for the formulation of transdermal dosage forms. Any suitable method or methods of conversion can be utilized to transform the adhesive composition to a usable dosage form, and are known to those skilled in the art.

As a non-limiting example, the adhesive-drug-additive mixture in its uncured form can be coated on a suitable substrate and allowed to cure using thermal energy or actinic radiation. For the coating purpose, any suitable coating techniques such as hand-proofing, slot-dye, extrusion coating, knife-coating, roll coating, knife-over-roll, blade coating or gravure coating can be used, depending upon the viscosity and other flow properties of the adhesive mixture.

Any suitable substrate can be utilized for adhesive coating purpose, and the general requirement is adhesion to the adhesive layer and compatibility with the adhesive formulation components including solvents. Exemplary materials used as substrate for coating include polyesters, polycarbonates, polyurethanes, polypropylenes, polyamides, polyvinyl chloride, polyolefin, polyvinyl acetate, polyether ether ketone, aluminum foil, aluminized plastics, kraft paper, siliconized kraft paper, as well as non-woven materials, and films made from blends, copolymers and composites thereof, which may be treated suitably to improve adhesion to the adhesive layer. Commercially available backing substrates such as 3M CoTran and ScotchPak systems can also be used to advantage.

Additionally, the exposed surface of the adhesive is covered with a suitable protective layer which is removed just before application of the dosage form to skin. Such a layer is made of suitably treated plastics, paper, non-woven or metal foil such as it possesses a release property that enables easy peel-off by the user before application, but protects accidental exposure of the adhesive surface while in storage. Examples of such release liners include silicone and fluorosilicone coated polyethylene, polypropylene, polyester, polyamide, Kraft paper, as well low density polyethylene which exhibits very low adhesion to silicone adhesives.

Optionally, the transdermal dosage forms include suitable rate-limiting membranes between the adhesive layer and the skin, in order to limit the release rate of active agents from the adhesive layer. Examples of such membranes include those made from polyurethanes, polysulfones, polyethersulfones, polyamides, polyvinyl acetates as well as copolymers of ethyl vinyl acetate.

The transdermal dosage form comprising the silicone adhesive can be used for passive delivery of incorporated drug, or the drug or active agent can be delivered using assisted-delivery techniques. Examples of assisted or active delivery include electrical-assisted drug delivery or iontophoresis which involves applying an electromotive force to the drug-in-adhesive layer that drives the drug molecule in the skin, ultrasound-assisted drug delivery, in which ultrasonic energy is used to enlarge skin pores and drive drug molecules into the skin, as well as use of localized thermal ablation methods and microneedles in conjunction with the drug-in-adhesive layer.

EXAMPLES

Example 1

Synthesis of Sulfonated Ionic Silicone Bearing Terminal Vinyl Groups

A three necked 500 mL flask was charged with 70.08 g (60.0 mmol) alpha-methylstyrene and $10.0 \times 10^{-4}$ g platinum catalyst. The temperature of the resulting mixture was brought to 115° C., then 30.0 g (120.5 mmol) 1,3,5,7-tetramethylcyclotetrasiloxane was added drop wise and continued to stir. The progress of the reaction mixture was monitored by $^1$H NMR. After 12 h of the reaction, complete conversion of silicone hydride was indicated by the NMR. Then, the reaction mixture was vacuum stripped at 150° C. for 2 h to remove unreacted alpha-methylstyrene which gave 80.5 g aralkylene substituted cyclotetrasiloxane. (Yield: (95%))

To 14.24 g (20.0 mmol) of the above aralkylene substituted cyclotetrasiloxane, 18.64 g (160.0 mmol) chlorosulfonic acid dissolved in 4.0 mL dichloromethane was added drop wise through a period of 30 minutes while the mixture being stirred at room temperature. The resulting mixture was continued to stir for an additional 30 minutes. The completion of the reaction was indicated by $^1$H NMR where complete sulfonation of the aromatic ring was indicated by the disappearance of para-substituted aromatic proton peak. The vacuum stripping of the reaction mixture at low pressure afforded 20.6 g of the sulfonic acid functional cyclotetrasiloxane as brown viscous gum. $^1$H NMR and $^{29}$Si NMR confirmed the product formation.

To the sulfonic acid functional cyclotetrasiloxane 5.7 g (8.0 mmol) obtained as above, 474.7 g (1600.0 mmol) octamethyltetracyclosiloxane and 1.48 g (8.0 mmol) 1,1,3,3-tetramethyl-1,3-divinyldisiloxane were added and continued to stir at room temperature. After reaching equilibrium of ~87 wt % of the linear siloxanes, the reaction mixture was neutralized using 10.0 g (128.0 mmol) moistened sodium bicarbonate at 70° C. The vacuum stripping of the reaction mixture at low pressure afforded 411.0 g of the product as a viscous gum. The NMR analysis of the product indicated that the polymer is vinyl-terminated sulfonated polydimethylsiloxane. (Yield: 84%)

Example 2

Synthesis of Sulfonated Ionic Silicone with End-Capped Sulfonate Groups

A three necked 500 mL flask was charged with 18.16 g (154.0 mmol) alpha-methylstyrene and $27.2 \times 10^{-5}$ platinum catalyst. The temperature of the resulting mixture was brought to 115° C., then 9.40 g (70.0 mmol) 1,1,3,3 tetramethyldisiloxane was added drop wise and continued to stir until completion of the hydrosilylation reaction. The complete hydrosilylation was indicated by the disappearance of silicone hydride peak in the $^1$H NMR. The resulting mixture was vacuum stripped to remove unreacted alpha-methylstyrene by placing on an oil bath at 150° C. for 2 h which gave 23.2 g aralkylene substituted disiloxane.

To this aralkylene substituted disiloxane (23.2 g, 62.4 mmol), 29.6 g (252.8 mmol) of chlorosulfonic acid was added drop wise through a period of 30 minutes while the mixture being stirred at room temperature. The resulting mixture was continued to stir for additional 30 minutes. The completion of the reaction was determined by $^1$H NMR where total sulfonation of the aromatic ring was indicated by the disappearance of para-substituted aromatic proton peak. The vacuum stripping of the reaction mixture at low pressure afforded 33.0 g of the sulfonated disiloxane as brown viscous oil.

To the sulfonic acid functional disiloxane 8.38 g (15.8 mmol) obtained in as above, 468.63 g (1580.0 mmol) octamethyltetracyclosiloxane was added and continued to stir at room temperature. After reaching an equilibrium of ~87 wt % of the linear siloxanes, the reaction mixture was neutralized using 10.6 (126.0 mmol) moistened sodium bicarbonate at 70° C. The vacuum stripping of the reaction mixture at low pressure afforded 541.4 g of the product as viscous gum. The NMR analysis of the product indicated that the polymer was a salt of terminal sulfonic acid functional polydimethylsiloxane. The polymer had a viscosity of 26.5 Pas at a shear rate of 10 rad/s when measured by a HAAKE Rheometer at 20° C.

Example 3

Synthesis of Calcium Carbonate Functional Polyorganosiloxane

A 500 ml three necked round bottom flask was charged with 650 ml water and 184 g (3.27 M) potassium hydroxide. 164.2 g (1 M) eugenol was added and the solution was heated to 90° C. and stirred till the solution become clear. 154.34 g (1.6 M) chloroacetic acid was dissolved in 320 ml water and added to above solution at 90-95° C. in about 3-4 hr. The solution was further stirred for about 2 h at 90-95° C., cooled to 50° C., acidified with dilute HCl and filtered the precipitate to give the carboxylic acid functional eugenol. A 2 L round bottom flask was charged with 177.76 g (0.8 M) of above product, 136 g (0.8 M) Iodopropane and 148 g (0.8 M) tributylamine was added to 1000 ml toluene. The solution was heated to 90° C. and stirred for 6 h. The solution was cooled to room temperature and the precipitate was filtered. The filtrate was stripped off the solvent to get the propyl ester of carboxylated eugenol. A 500 ml three necked round bottom flask was charged with 185 g (0.7 M) above compound, 46.9 g (0.35 M) tetramethyldisiloxane and 0.05 g Pt Karstedt's catalyst. The solution was stirred for 120 h at 68-70° C. to get the carboxylate ester disiloxane derivative. A 500 ml three necked round bottom flask was charged with 66 g above compound and 250 ml ethyl alcohol. Aqueous sodium hydroxide solution (12 g sodium hydroxide in 50 ml water) was added and the solution was stirred for 3 h at 70° C. to give the carboxylic acid functional tetramethyldisiloxane derivative. A 500 ml three necked round bottom flask was charged with 20 g (0.034 M) above compound, 504 g (1.7 M) octamethylcyclotetrasiloxane and 8 g acidic ion exchange resin. The solution was stirred for 40 h at 70-75° C. to give the carboxylic acid functional polydimethylsiloxane. A 500 ml three necked round bottom flask was charged with 152.96 g (0.01 M) above compound and 0.56 g (0.01 M) calcium oxide. The solution was stirred for 16 h at 50-55° C. to give calcium carboxylate functional polyorganosiloxane.

The calcium carboxylate functional polyorganosiloxane obtained in this manner possessed adhesive property.

Example 4

Sulfonated Functionalized Polyorganosiloxanes Bearing Terminal Acrylate Groups

A three necked flask was charged with 354.0 g (3000.0 mmol) of alpha-methyl styrene, and $5.04 \times 10^{-3}$ g of Speier's catalyst. The resulting mixture was heated to 115° C. while stirring under positive nitrogen flow. To this 150.0 g (625.0 mmol) 1,3,5,7 tetramethylcyclotetrasiloxane was added gradually. The progress of reaction was monitored by $^1$H NMR for the disappearance of silicone hydride peak. After completion of reaction, the reaction mixture was vacuum stripped at low pressure to remove unreacted alpha-methyl styrene to give 424 g (84%) aryl substituted cyclotetrasiloxane, and the structure was confirmed via NMR.

To 5.0 g (7.0 mmol) of above aryl substituted cyclotetrasiloxane, 10 ml of dichloromethane was added, and under vigorous stirring at room temperature 6.54 g (56.0 mmol) of chlorosulfonic acid was added gradually. The resulting viscous mixture was stirred for additional 45 minutes. To this 155.2 g (526.6 mmol) of octamethyltetracyclosiloxane and 1.88 g (14.0 mmol) of 1,1,3,3 tetramethyldisiloxane was added and continued to stir at room temperature. After reaching at solid content of 80%, the reaction mixture was neutralized using 9.43 g (112.0 mmol) moistened sodium bicarbonate at 75° C. The vacuum stripping of reaction mixture at 120° C. afforded 148 g (83%) the product. The NMR analysis of the product indicated that the polymer is a sulfonated polydimethylsiloxane with terminal hydride groups.

To 50.0 g (4.7 mmol) of sulfonated functionalized polyorganosiloxanes with terminal hydride group as obtained above, 150 ml toluene was added and the reaction mixture was heated to 80° C. At this point $8.08 \times 10^{-3}$ g of speier's catalyst was added and the reaction mixture was further heated to 105° C. To this 2 g (11.29 mmol) of vinylcyclohexyl epoxide was added gradually. The reaction was monitored with $^1$H NMR for the disappearance of silicone hydride peak. After completion of reaction, the reaction mixture was vacuum stripped to yield 48 g (94%) of sulfonate functionalized silicone with terminal epoxy group.

To 48.0 (4.33 mmol) of sulfonate functionalized silicone with terminal epoxy group, 100 ml of toluene was added and the reaction mixture was heated to 90° C. To this mixture $4.88 \times 10^{-2}$ g of titanium isopropoxide and 5 mg 2,2,6,6-tetramethyl-1-piperidinoxyl (TEMPO) was added. The reaction mixture was further heated to 105° C. and then 0.748 g (10.39 mmol) of acrylic acid was added gradually. The reaction mixture was monitored with $^1$H NMR for the disappearance of epoxy peak. After completion of reaction, the reaction mixture was vacuum stripped at 40° C. to yield 45 g of sulfonate functionalized silicone with terminal acrylate group.

Example 5

Polymer Composite Silicone Adhesive from Pendant-Sulfonated Polydiorganosiloxane and Condensed Tetraethylorthosilicate The vinyl-terminated, pendant sulfonated silicone ionomer was mixed with tetraethyl orthosilicate (TEOS) with TEOS content varying from 1 wt % to 10 wt % of the total composition. The two compounds were mixed thoroughly in a high-speed mixer (2200 RPM) and formed a uniform blend. To this blend, the catalyst dibutyl tin dialaurate (DBTDL) was added at 0.5 wt % and the mixture was homogenized again. Following the mixing, the blend was poured in Teflon molds and allowed to cure overnight.

Upon curing, translucent films were obtained, which had varying degrees of tack. The level of tackiness decreased with increasing TEOS content. The blend with control vinyl PDMS did not cure to form a film, indicating the contribution of ionic aggregation to film mechanical strength.

Example 6

Polymer Composite Silicone Adhesive from End-Sulfonated Polydiorganosiloxane and Condensed Tetraethylorthosilicate The end-sulfonated silicone ionomer or a control vinyl-modified siloxane (U10, Momentive Performance Materials) was mixed with tetraethyl orthosilicate (TEOS) with TEOS content varying from 5 wt % to 25 wt %. A suitable solvent (ethyl acetate, hexane or toluene) was added to increase processibility. The components were mixed thoroughly in a high-speed mixer (2200 RPM) and formed a uniform blend. To this blend, the catalyst dibutyl tin dilaurate (DBTDL) was added at concentrations ranging from 0.2 to 0.5 wt % of total solids and the mixture was homogenized again. Following the mixing, the blend was cast either as 200 micron films on a polyethylene sheet using an automated draw-down machine, or poured into Teflon molds. The films were cured overnight and the solvent was evaporated. Upon curing, translucent films were obtained, which had varying degrees of tack, as determined by finger-touch. The level of tackiness decreased with increasing TEOS content. The films with 25% initial TEOS loading did not demonstrate any tack. Further, the blend with control vinyl PDMS did not cure to form a film, indicating the contribution of ionic aggregation to film mechanical strength.

Example 7

Silver Release from Polymer Composite Silicone Adhesive of End-Sulfonated Polydiorganosiloxane and Condensed Tetraethylorthosilicate Polymer composite silicone adhesive of sodium salt of end-sulfonated polydiorganosiloxane were prepared as described in Example 5, using a varying initial TEOS loading of 5 wt % to 25 wt % and with DBTDL loading of 0.2%. The films were contacted with 1.1 wt % of silver nitrate solution prepared in $HNO_3$-acidified DI water, during which the sodium ions from the polydiorganosiloxane are replaced with silver ions. The films were immersed in the silver nitrate solution for 48 h, washed with copious amounts of DI water and dried for 24 h at 50° C. The films were immersed in 0.1M sodium nitrate solution and aliquots removed at specific intervals. The silver ion content in the aliquots was analyzed by ICP (Inductively Coupled Plasma) spectroscopy. The cumulative amount of releases of silver ions as a function of time is shown in FIG. 1.

Example 8

Figure 2:
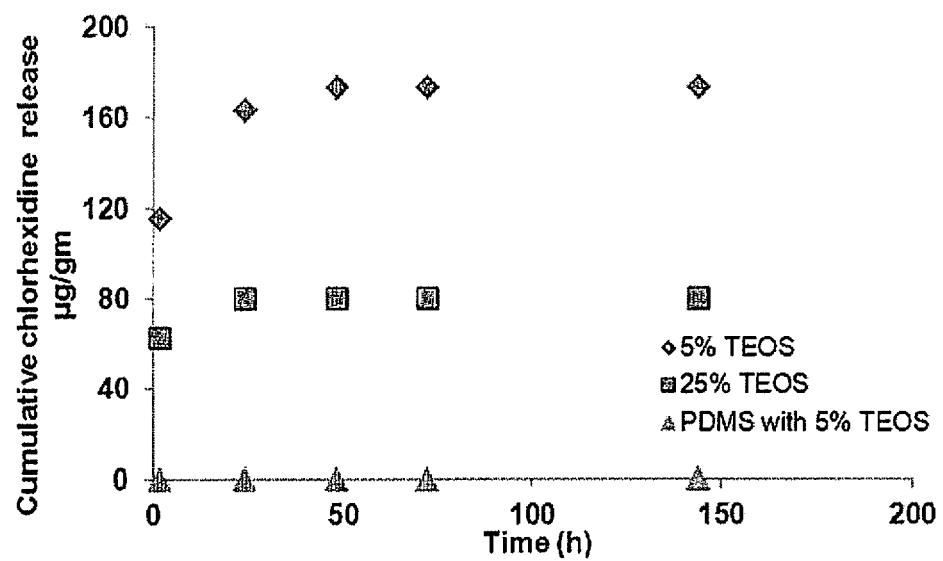
FIG. 2 is a graph illustrating the release of chlorhexidine from the polymer composite silicone adhesive of Example 8.

Chlorhexidine Release from Polymer Composite Silicone Adhesive Comprising End-Sulfonated Polydiorganosiloxane and Condensed Tetraethylorthosilicate Polymer composite silicone adhesives of sodium salt of end-sulfonated polydiorganosiloxane (Example 2) were prepared as described in Example 6, using a varying initial TEOS loading of 5% and 25% and with DBTDL loading of 0.5 wt % of total solids. The films were contacted with a solution of 20% chlorhexidine digluconate. As a control, silanol-terminated PDMS film, crosslinked using 5% TEOS was used. The films were immersed for 48 h, washed with copious amounts of DI water and dried for 24 h at 50° C. The films were immersed in 50 mM sodium acetate buffer, pH 5.5, and aliquots removed at timed intervals. The chlorhexidine (CHX) content was analyzed by liquid chromatography. The cumulative amount of releases of CHX as a function of time is as shown. As can be seen, the non-ionic PDMS film did not bind and release any amount of CHX (FIG. 2).

Example 9

Antimicrobial Activity of Polymer Composite Silicone Adhesive from Vinyl-Functionalized, Pendant-Sulfonated Polydiorganosiloxane and Condensed Tetraethylorthosilicate Containing Silver Polymer composite adhesives of vinyl-functional pendant sulfonated polydiorganosiloxane were prepared and loaded with silver as described in Example 7. The films were then tested for antimicrobial activity using the AATCC Method 100 technique, using *E. coli* and *S. aureus* as representative gram negative and gram positive test organisms respectively. An adhesive sheet that was not contacted with silver was also used as a negative control. Upon 24 h contact time, the silver-contacted sheet resulted in greater the 5 log reduction of *E. coli* counts and close to 4 log reduction in *S. aureus* counts. The control film did not demonstrate any significant antimicrobial activity within the contact time.

Example 10

Rheological Characterization of Polymer Composite Silicone Adhesives Comprising Pendant-Sulfonated Polydiorganosiloxane and Condensed Tetraethyl Orthosilicate Pressure sensitive adhesives (PSA) were prepared as described in Example 5, with TEOS content varying from 10 wt % to 25 wt % and at a catalyst loading of 0.5 wt %. The viscoelastic properties of the adhesive sheets (1-1.5 mm thickness) were tested using a Haake-Rheostress oscillatory rheometer using a cone-and-plate attachment (1° angle) and a gap width of 0.052 mm optimized for this testing geometry. Each adhesive sample was first subjected to an increasing oscillatory stress ranging from 100 to 10,000 Pa at a fixed frequency (1 Hz) to identify the linear viscoelastic region (LVR). Afterwards, the samples were subjected to a suitable oscillatory stress within the LVR but the frequency was varied from 0.01 to 100 Hz. In each case, the storage (G') and loss moduli (G") were measured as a function of applied stress or frequency. Based on these measurements, it was determined whether the pressure sensitive adhesives satisfy the modified Chu criteria for viscoelasticity, which are G' (0.1 Hz) between $0.5 \times 10^4$ to $5 \times 10^4$ Pa and the ratio G' (100 Hz)/G' (0.1 Hz) lies between 5 and 300. {Ref: Ho and Dodou, Int. J. Pharmaceutics 333 (2007) pp 24-33}

Figure 3A:
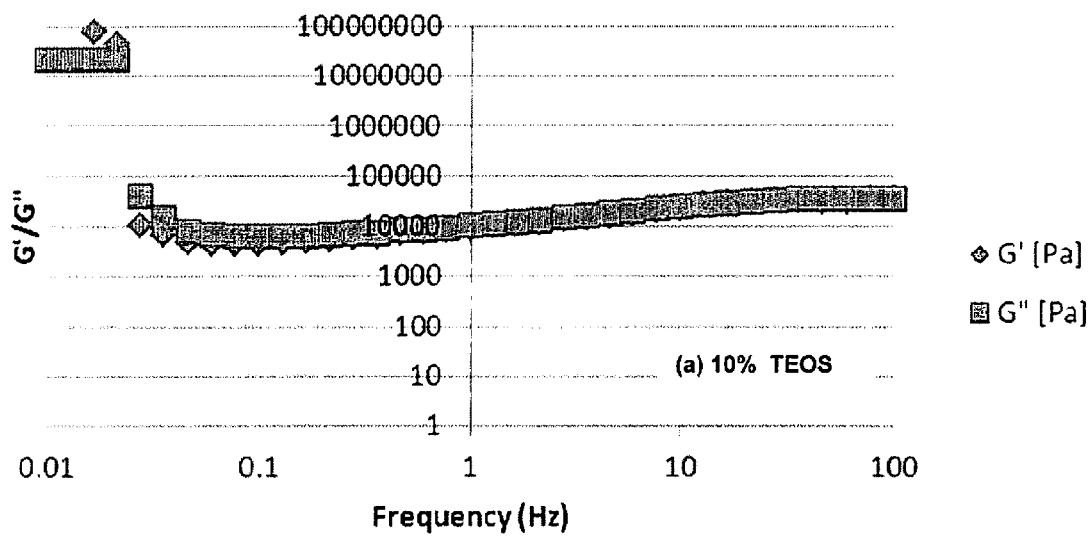
FIGS. 3(a) and 3(b) are graphs illustrating the rheological characterization of polymer composite silicone adhesive of Example 10.
Figure 3B:
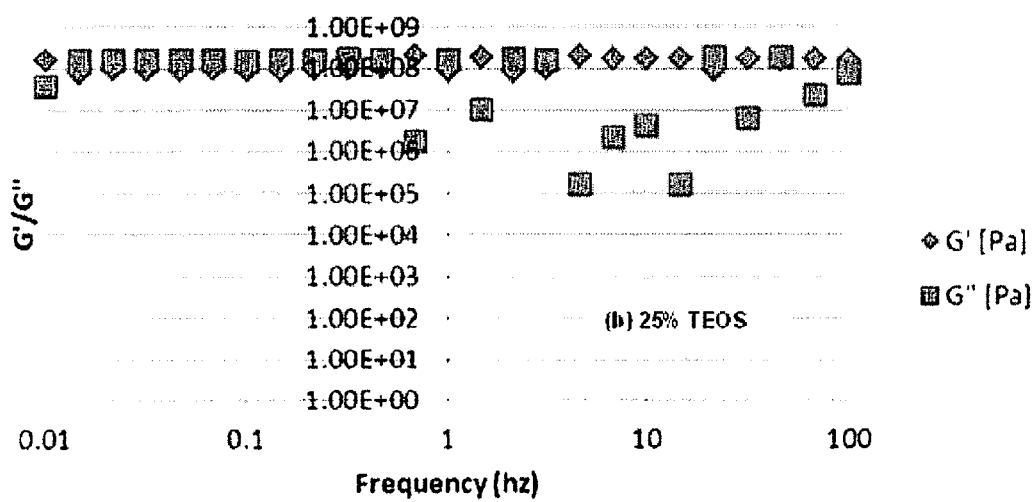

The results of the viscoelastic measurement (frequency sweep) are shown below. It can be seen that, from these graphs, the 25 wt % TEOS adhesive formulation does not meet the Chu criteria, whereas the 10 wt % TEOS formulation marginally satisfies the viscoelastic requirements of a PSA applicable for transdermal delivery of active agents (FIG. 3).

Example 11

Polymer Composite Silicone Adhesive for Transdermal Delivery of Ibuprofen

Figure 4:
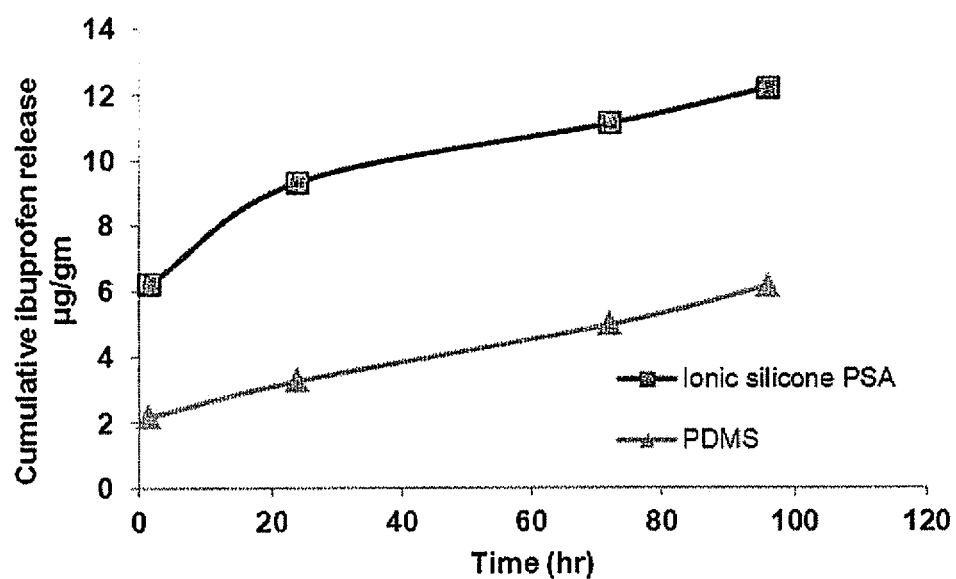
FIG. 4 is a graph illustrating the release of ibuprofen from the polymer composite silicone adhesive of Example 11.

Sustained release of the model drug ibuprofen was studied from ionic silicone PSA. Polymer composite adhesives were prepared as described in Example 5, with 10% TEOS content and at a DBTDL catalyst loading of 0.5 wt %. The drug ibuprofen was incorporated by dissolving the drug in the solvent (toluene) used for mixing the ionic polydiorganosiloxane, crosslinker and catalyst. Ibuprofen loading was 1 wt % of drug based on total solids. Upon mixing, the drug-containing mixtures were poured in Teflon molds and allowed to cure overnight. A silanol-PDMS film crosslinked with 5% TEOS was also loaded with 1% ibuprofen and served as a control. The resulting films were cut in samples, weighed and immersed in a mixture of 25% IPA/75% DI water to measure the drug release rate. Aliquots were removed at pre-determined time intervals and ibuprofen content was analyzed using HPLC. It was observed that there was a marked difference in the absolute amount of ibuprofen release from the ionic silicone-containing formulation, and that from the PDMS-containing film (FIG. 4).

The difference in release rate of ibuprofen from the ionic silicone formulation could be due to the difference in the interaction of the drug and the ionic silicone or control PDMS.

To further study the interaction, the drug containing samples were analyzed via DSC using a TA Instruments Differential Scanning Calorimeter. The ionic silicone and PDMS-based samples containing ibuprofen, as well as pure drug were heated from room temperature to 200° C. at a rate of 5° C./min. The drug melting point, Tm was identified at 77° C. For the drug containing ionic silicone based PSA, the melting transition was not seen in the range tested, whereas for the PDMS-based film, a melting peak was observed at 74° C. This indicates that in the ionic silicone environment, the drug is either dissolved in the solid polymer, or remains in amorphous form but the drug crystallizes or precipitates in the PDMS environment. This evidence of differential interactions could explain the difference in ibuprofen release through these systems (FIGS. 5(b) and (c)).

Example 12

Addition Curable Silicone Adhesive

Varying amounts of the sulfonate functional polydiorganosiloxane bearing terminal vinyl groups (Example 1) was blended with vinyl-terminated PDMS (U1, 1 Pa·s viscosity, Momentive), hydride-functional PDMS crosslinker (Vern 230, Momentive), and hydride terminated PDMS chain extender (TP 3359, Momentive) inhibitor (1,3, divinyldimethylsiloxane, MviMvi) and blended in a high speed mixer. Platinum catalyst was added to this mixture and it was poured in suitable polystyrene molds or drawn as a thin film on a PET release liner followed by curing at room temperature. Upon curing, a soft, tacky composition was obtained. The crosslinker and chain extender content was varied such that the ratio of silicone hydride groups to vinyl silicone groups ranged from 0.477 to 1 (Example 12a to 12c), which gives compositions with varying softness and tack.

TABLE 1

Addition Cure adhesives comprising sulfonate functional silicone ionomer

| Component (gm) | Control | Example 12a 25/75 Ex1/U1 | Example 12b 50/50 Ex1/U1 | Example 12c 90/10 Ex1/U1 |
|---|---|---|---|---|
| U1 | 23.809 | 17.857 | 11.905 | 2.380 |
| Vinyl-functional sulfonated silicone | 0 | 5.952 | 11.905 | 21.428 |
| Pt-D | 0.0125 | 0.0125 | 0.0125 | 0.035 |
| Divinyl dimethyl siloxane | 0.001 | 0.001 | 0.001 | 0.001 |
| Vern 230 | 0.463 | 0.377 | 0.291 | 0.244 |
| TP 3359 | 0.304 | 0.304 | 0.304 | 0.5 |
| SiH/ViSi ratio | 0.5 | 0.5 | 0.5 | 0.8 |

Example 13

Water Uptake of Addition Curable Silicone Adhesive

Figure 6A:
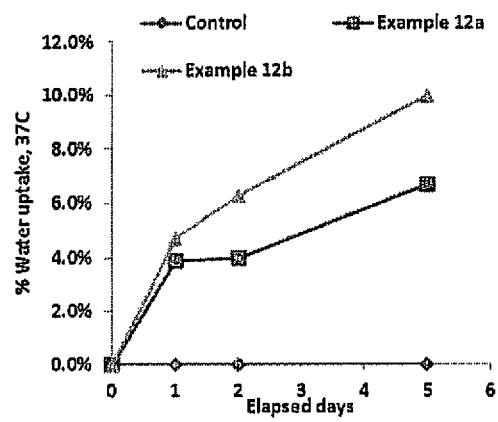
FIGS. 6(a) and 6(b) are a series of graphs illustrating the absorption of water by the addition curable silicone adhesive of Example 12.
Figure 6B:
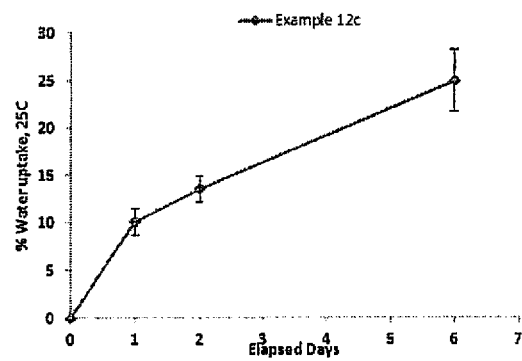

The silicone ionomer containing adhesives, Control, Example 12a and Example 12b were weighed and incubated in simulated wound fluid (142 mM NaCl, 2.5 mM $CaCl_2 \cdot 2H_2O$ in DI water) at 37 C, as per the British Standard BS EN 13726-1:2002 (Test methods for primary wound dressings—Part 1: Aspects of absorbency). The gel of Example 12c was incubated in DI water at ambient temperature. At varying time intervals, the gel samples were blotted dry and weighed. The percentage increase in weight, corresponding to imbibition of water by the adhesive was calculated as water uptake. The water uptake by the adhesive was found to be proportional to their silicone ionomer content, and progressively increased with the incubation period (FIGS. 6(a) and 6(b)).

Example 14

Tack Measurement of Addition Curable Silicone Adhesive

The silicone ionomer containing addition curable adhesives Control, Example 12a and Example 12b were cast as circular sheets of 2 mm thickness and 60 mm diameter in polystyrene molds. Upon curing, the adhesive sheets were post-cured at 50° C. for 2 h, de-molded and the tack was measured using a Dia-Stron Miniature tensile tester (MTT 175) equipped with the parallel plate attachment. Briefly, the adhesive sheet was placed on the lower stainless steel plate, which is connected to the force transducer of the instrument. The upper plate was aligned, and the gel sheet was pressed by the instrument's force arm at a load of 50 g for 20 seconds, following which it was pulled upwards at a rate of 100 mm/min. The amount of force required to separate the top plate from the gel was measured by the force transducer as a function of separation distance, and the peak value encountered is reported as tack force. The test was repeated for twenty cycles per sample, and each adhesive sample was tested in duplicate. It was found that a statistically significant reduction of tack occurred upon the incorporation of silicone ionomers within the addition curable adhesives.

TABLE 2

Peak tack force measurement of addition curable silicone adhesive

| Formulation | Peak tack force (gmf) |
|---|---|
| Control | 308 ± 30 |
| Example 12a | 290 ± 39 ($p < 0.05$ vs control, two parameter t-test) |
| Example 12b | 250 ± 12 ($p < 0.05$ vs control $p > 0.05$ vs 25% two parameter t-test) |

Example 15

Measurement of Moisture Vapor Transport of Addition Curable Silicone Adhesive

Figure 7:
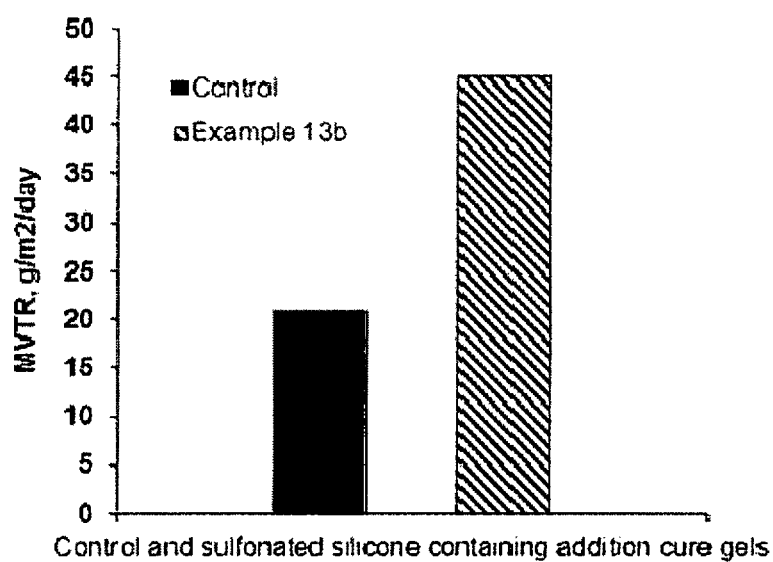
FIG. 7 is a graph illustrating the moisture vapor transport rate of the addition curable silicone adhesive of Example 12.

The moisture vapor transport property of the silicone ionomer containing addition curable adhesives was measured as per the British Standard BS EN 13726-1:2002 (Test methods for primary wound dressings—Part 1: Aspects of absorbency). The adhesive samples Control, and Example 12b were used in form of circular sheets of 2 mm thickness. An apparatus similar to the Paddington Cups (Surgical Materials Testing Laboratory, Cardiff, UK) were used. The apparatus consists of an aluminum cup open at both ends. The adhesive samples were clamped on one end of the cup using an aluminum flange with a known orifice area. The cup was filled with a known quantity of DI water and the remaining end was closed with a blind flange. Vacuum grease was applied at all flange connections to prevent moisture loss. The closed assembly was weighed and placed in an 'Inverted position' (water in contact with the adhesive sheet), in a constant temperature (25° C.) and humidity (50% RH) environment. Periodically the assembly was weighed and any loss was attributed to the transport of water vapor through the gel sheet. The average daily water vapor loss (in $g/m^2/day$) was estimated from the slope of the weight loss vs. time elapsed curve. Each adhesive formulation was tested in triplicate. Incorporation of ionic silicones resulted in a two-fold increase in moisture vapor transport rate (FIG. 7).

Example 16

Antimicrobial Activity of Addition Curable Silicone Adhesive

An addition curable silicone adhesive composition comprising sulfonate functional polydiorganosiloxane bearing terminal vinyl groups (Example 1) and a Control a was prepared as per the following Table:

TABLE 3

| Component | Ionic silicone formulation (wt in gm) | Control (wt in gm) |
|---|---|---|
| U10 (Vinyl-terminated PDMS, 10 Pa-s) | 0 | 4.028 |
| U1 (Vinyl-terminated PDMS, 1 Pa-s) | 0 | 4.888 |
| Vinyl functional sulfonated silicone | 9.50 | 0 |
| Pt-D catalyst | 0.042 | 0.04 |
| MGT 2364 (Vinyl terminated PDMS) | 0.300 | 0.197 |
| Vern 140 (Si—H Crosslinker) | 0.04 | 0.218 |
| TP 3359 (Si—H Chain extender) | 0.7 | 0.663 |
| SiH/Si-vi | 1.11 | 1.11 |

Figure 8:
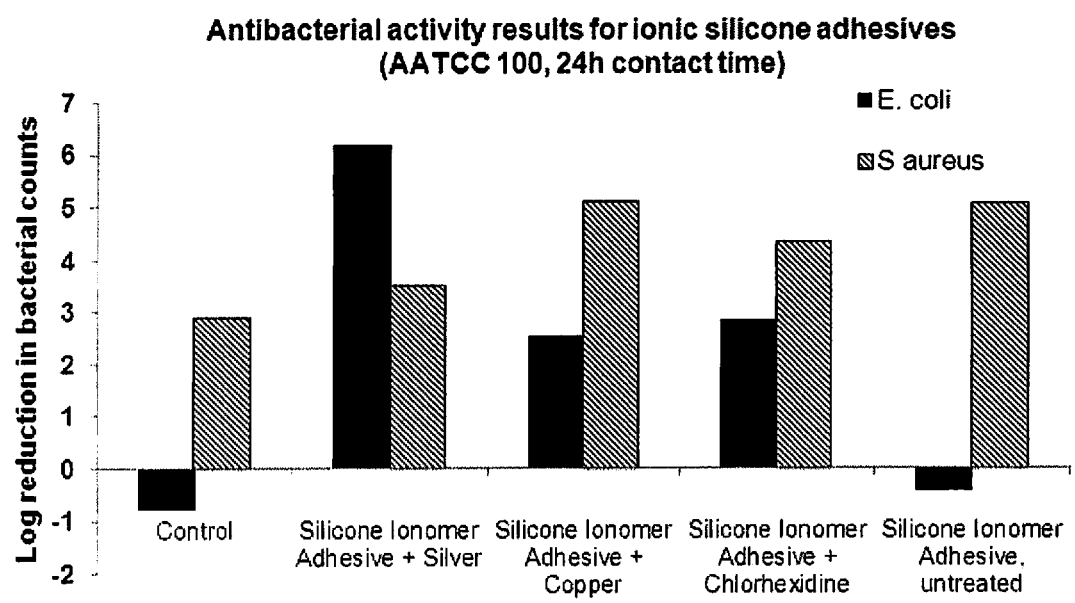
FIG. 8 is a graph indicating the antimicrobial activity of the addition curable silicone adhesives of Example 16.

The compositions were cast as thin films (coat weight 0.23 g/in$^2$) on polyester sheets, and cured overnight at room temperature to form adhesive films. The silicone ionomer adhesive films were cut into coupons and immersed separately into solutions of $AgNO_3$ (0.1M in DI water), $CuSO_4$ (0.1M in DI water), Chlorhexidine digluconate (20% in water) or DI water only, for a period of 48 h. The Control adhesive films without silicone ionomer were left untreated. After the above treatment, the coupons were rinsed with copious amounts of DI water and dried overnight in a hot-air oven at 70° C. The coupons were then tested for antimicrobial activity using the AATCC Method 100 technique, using *E. coli* and *S. aureus* as representative gram negative and gram positive test organisms respectively. The log reductions from initial CFU (10$^6$/ml) for the films for 24 h contact time are as shown in FIG. 8.

It can be seen that silver nitrate treated adhesives showed a maximum of reduction in *E. coli* bacterial counts.

Example 17

Testosterone Release from Addition Curable Silicone Adhesive

Testosterone loaded (2 wt %) addition curable silicone adhesive composition and a control PDMS adhesive were prepared having the following overall composition were prepared as shown:

TABLE 4

| Component | Ionic silicone formulation (wt in gm) | Control (wt in gm) |
|---|---|---|
| U10 (Vinyl-terminated PDMS, 10 Pa-s) | 0 | 4.028 |
| U1 (Vinyl-terminated PDMS, 1 Pa-s) | 0 | 4.888 |
| Vinyl functional sulfonated silicone | 9.5 | 0 |
| MviMvi (Inhibitor) | 0.02 | 0.02 |
| Pt-D catalyst | 0.042 | 0.04 |
| MGT 2364 (Vinyl terminated PDMS) | 0.3 | 0.197 |
| Vern 140 (Si—H Crosslinker) | 0.04 | 0.218 |
| TP 3359 (Si—H Chain extender) | 0.7 | 0.655 |
| SiH/Si-vi | 1.1 | 1.1 |

To incorporate the drug, a pre-determined amount of testosterone was dissolved in 3 ml THF. To this was added the MGT 2364, Vern 140, MviMvi and TP 3359. The mixture was stirred on a high-speed mixer for 2.3 min at 2000 RPM. Then, U1 and U10 or silicone ionomer were added to the respective drug mixtures, and the composition was stirred again on the high speed mixer for 7 min at 2300 RPM. After this step, the catalyst and inhibitor were added to both the formulations and mixed for 1.15 min at 2000 RPM. An equal amount of each of the drug-silicone mixtures were cast in circular polypropylene molds, and kept undisturbed overnight for curing and removal of residual THF.

Figure 9A:
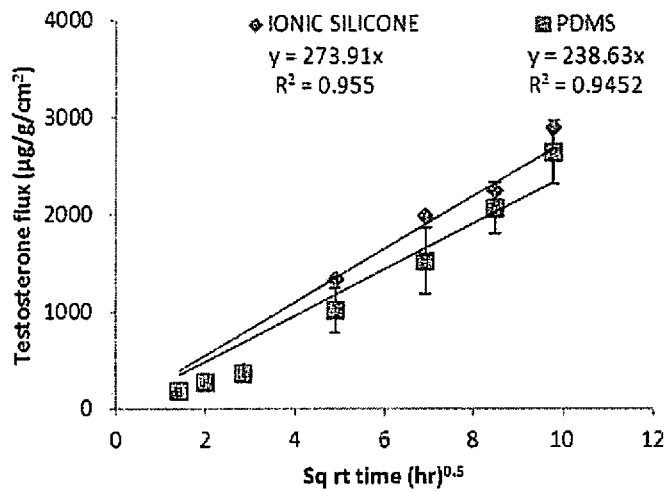
FIG. 9(a) is a graph indicating the release of testosterone from the addition curable silicone adhesive of Example 17.
Figure 9B:
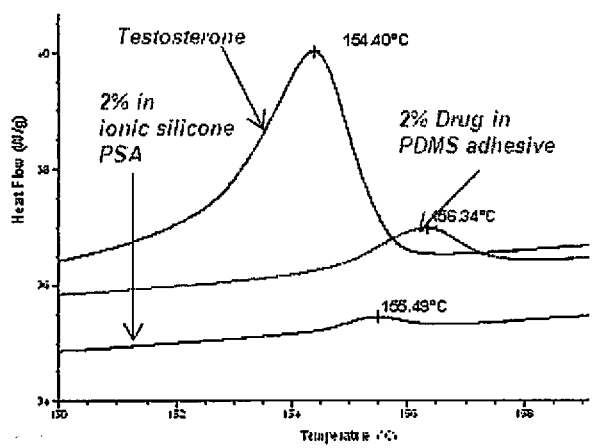
FIG. 9(b) is a graph indicating differential scanning calorimetry of the addition curable silicone adhesive of Example 17.

Upon curing the samples were tested for release of testosterone in a solution of 40% PEG400, 137 mM NaCl, for a period of up to 96 h. The normalized drug flux resulting from the exposed area of the mold was calculated and plotted as a function of square root of the respective time of sampling. The data showed an excellent fit to the Higuchi equation. Based on the calculated slope of the release curve, a 15% increase in drug release rate was seen in case of silicone ionomer based adhesive formulation (FIG. 9(*a*)).

The difference in drug compatibility with the ionic silicone adhesive vis-á-vis the PDMS adhesive was determined via DSC as described in Example 12 above. The free drug, and drug loaded PDMS and ionic silicone adhesive were subjected to a heating and cooling cycle under air atmosphere. The DSC thermograms are show in FIG. 9(*b*).

From the thermogram a distinct melting peak for the drug is seen at 154.4° C. For the adhesive formulations the melting peak was seen to be shifted slightly. Also, the peak area for the ionic silicone-based formulation was found to be lower than the peak for PDMS adhesive.

To quantify the result and the difference in compatibility, the areas were calculated as normalized heat of melting of drug crystals present in the formulation. The values were attributed to the solid fraction of distinct drug crystals present in the formulation, and the following results were obtained:

TABLE 5

| Sample | Heat of Melting (J/gm) | % Solid drug fraction |
|---|---|---|
| Testosterone | 73 | 100% (assigned) |
| 2% Testosterone in PDMS adhesive | 1.9 | 2.6% |
| 2% Testosterone in ionic silicone adhesive | 0.35 | 0.5% |

This shows that most of the drug loaded in PDMS adhesive was crystallized, whereas a lesser amount was present as crystals in ionic silicone adhesive, indicating better compatibility of testosterone with ionic silicone.

Example 18

Diclofenac Sodium Release from Addition Curable Silicone Adhesive

Diclofenac Sodium loaded (1 wt %) silicone ionomer adhesive composition and a control PDMS adhesive were prepared having the following overall composition:

TABLE 6

| Component | Ionic silicone formulation (wt in gm) | Control (wt in gm) |
|---|---|---|
| U10 (Vinyl-terminated PDMS, 10 Pa-s) | 0 | 2.014 |

TABLE 6-continued

| Component | Ionic silicone formulation (wt in gm) | Control (wt in gm) |
|---|---|---|
| U1 (Vinyl-terminated PDMS, 1 Pa-s) | 0 | 2.444 |
| Vinyl functional sulfonated silicone | 4.75 | 0 |
| MviMvi (Inhibitor) | 0.02 | 0.02 |
| Pt-D catalyst | 0.021 | 0.02 |
| MGT 2364 (Vinyl terminated PDMS) | 0.15 | 0.099 |
| Vern 140 (Si—H Crosslinker) | 0.02 | 0.109 |
| TP 3359 (Si—H Chain extender) | 0.37 | 0.35 |
| SiH/Si-vi | 1.169 | 1.157 |

A pre-determined amount of solid drug was added to MGT 2364, Vern 140, MviMvi and TP 3359, followed by addition of 3 ml THF as solvent. The mixture was stirred on a high-speed mixer for 2.3 min at 2000 RPM. Then, U1 and U10 or silicone ionomer were added to the respective drug mixtures, and the composition was stirred again on the high speed mixer for 7 min at 2300 RPM. After this step, the catalyst and inhibitor were added to both the formulations and mixed for 1.15 min at 2000 RPM. An equal amount of each of the drug-silicone mixtures were cast in circular polypropylene molds, and kept undisturbed overnight for curing and removal of residual THF.

Upon curing the samples were tested for release of diclofenac sodium in a solution of 137 mM NaCl. The normalized drug flux resulting from the exposed area of the mold was calculated and plotted as a function of the respective time of sampling.

Figure 10:
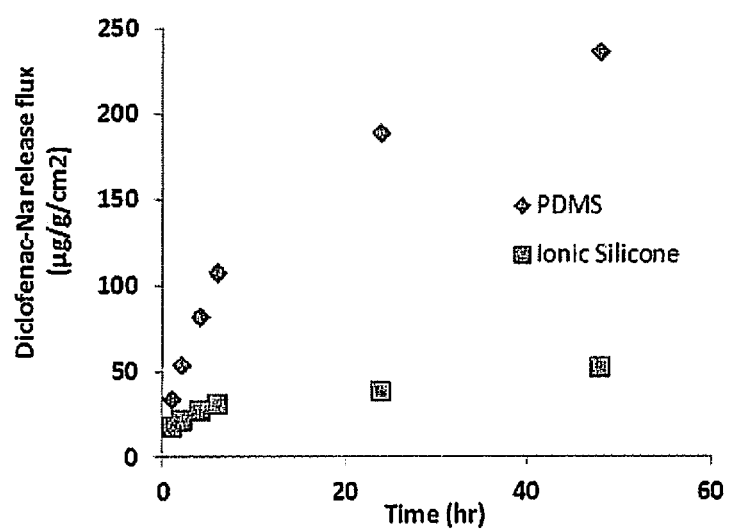
FIG. 10 is a graph indicating the release of diclofenac sodium from the addition curable silicone adhesive of Example 18.

It can be seen that in case of Diclofenac sodium, a higher release was seen with PDMS as opposed to ionic silicone (FIG. 10). Without being limited by the theory in any way, it can be hypothesized that due to its high water solubility, the drug is preferentially partitioned in the aqueous phase when it is loaded in the hydrophobic PDMS. However, when it is loaded in the comparatively more hydrophilic ionic silicone the preference for the aqueous phase is lower. This property of silicone ionomers can be exploited to develop sustained release formulations of highly hydrophilic drugs, which is challenging on account of their high water solubility which often results in a burst release effect.

Example 19

Dapsone Release from Addition Curable Silicone Adhesive

Dapsone loaded (1 wt %) silicone ionomer adhesive composition and a control PDMS adhesive were prepared having the following overall composition:

TABLE 7

| Component | Ionic silicone formulation (wt in gm) | Control (wt in gm) |
|---|---|---|
| U10 (Vinyl-terminated PDMS, 10 Pa-s) | 0 | 2.014 |
| U1 (Vinyl-terminated PDMS, 1 Pa-s) | 0 | 2.444 |
| Vinyl functional sulfonated silicone | 4.75 | 0 |
| MviMvi (Inhibitor) | 0.02 | 0.02 |
| Pt-D catalyst | 0.021 | 0.02 |
| MGT 2364 (Vinyl terminated PDMS) | 0.15 | 0.099 |

TABLE 7-continued

| Component | Ionic silicone formulation (wt in gm) | Control (wt in gm) |
|---|---|---|
| Vern 140 (Si—H Crosslinker) | 0.02 | 0.109 |
| TP 3359 (Si—H Chain extender) | 0.37 | 0.35 |
| SiH/Si-vi | 1.169 | 1.157 |

A pre-determined amount of solid drug was added to MGT 2364, Vern 140, MviMvi and TP 3359, followed by addition of 3 ml THF as solvent. The mixture was stirred on a high-speed mixer for 2.3 min at 2000 RPM. Then, U1 and U10 or silicone ionomer were added to the respective drug mixtures, and the composition was stirred again on the high speed mixer for 7 min at 2300 RPM. After this step, the catalyst and inhibitor were added to both the formulations and mixed for 1.15 min at 2000 RPM. An equal amount of each of the drug-silicone mixtures were cast in circular polypropylene molds, and kept undisturbed overnight for curing and removal of residual THF.

Upon curing the samples were tested for release of Dapsone in a solution of 50% PEG 400 and 137 mM NaCl. The normalized drug flux resulting from the exposed area of the mold was calculated and plotted as a function of the respective time of sampling.

Figure 11:
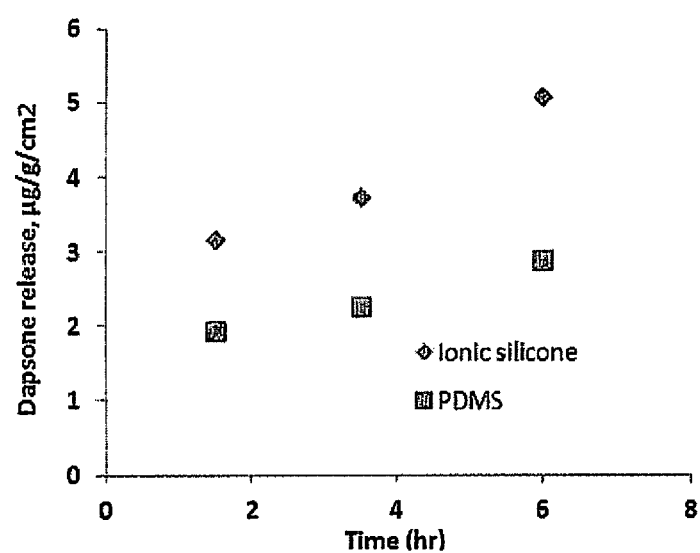
FIG. 11 is a graph indicating the release of dapsone from the addition curable silicone adhesive of Example 19.

It can be seen that in case of Dapsone, an antibacterial and antifungal compound, a higher release was seen with ionic silicone based formulation as opposed to PDMS (FIG. 11).

Example 20

UV Curable Addition Curable Silicone Adhesive

An addition curable silicone adhesive composition was prepared as per the following Table.

TABLE 8

| Component | Weight (gm) |
|---|---|
| Vinyl-functional sulfonated silicone | 5.0 |
| MGT 2364 | 0.150 |
| Divinyl dimethyl siloxane | 0.02 |
| Vern 140 | 0.1 |
| TP 3359 | 0.370 |
| SiH/viSi ratio | 4.06 |

The components were mixed together and the UV-activated addition cure catalyst Trimethyl($\eta^5$-methylcyclopentadienyl)platinum(IV) (STREM Chemicals) was added to the mixture. The mixture was then irradiated with UV-light of 320 nm wavelength (105 mW/cm$^2$) for 90 seconds, which resulted in complete curing of the mixture to result in a tacky adhesive.

Example 21

Preparation of Antimicrobial Addition Curable Silicone Adhesive from Ionic Silicone Antimicrobial Masterbatches Vinyl functional sulfonated silicone prepared as described was dissolved in hexane. This solution was contacted with 20% solution of chlorhexidine gluconate, or 1M copper sulfate to exchange the sodium ions with chlorhexidine or copper respectively. After 48 h contact time, the silicone containing organic phase was separated and washed with a 1:1 solution of methanol and water several times, to remove non-specifically bound copper and chlorhexidine gluconate. The organic phase was dried in a rotary evaporator to remove water and residual solvents.

Adhesive formulations were prepared from the masterbatches using the following components in quantities described as below.

TABLE 9

| Component | Weight (gm) |
|---|---|
| Vinyl-functional sulfonated silicone | 2.5 |
| MGT 2364 | 0.15 |
| Sulfonated silicone antimicrobial masterbatch | 2.5 |
| Vern 140 | 0.10 |
| TP 3359 | 0.37 |
| SiH/viSi ratio | 2.07 |

To this mixture, a suitable amount of UV-cure Pt catalyst was added and the mixture was cast on a PET sheet and cured using UV radiation at 105 mW/cm². The cured samples were analyzed for chlorhexidine content by estimation of nitrogen using C/H/N analysis. Copper content was estimated by digesting the adhesive using HF and analyzing the digest using ICP. A chlorhexidine content of 2.5 wt % and a copper content of 1 wt % were obtained using these techniques.

Figure 12A:
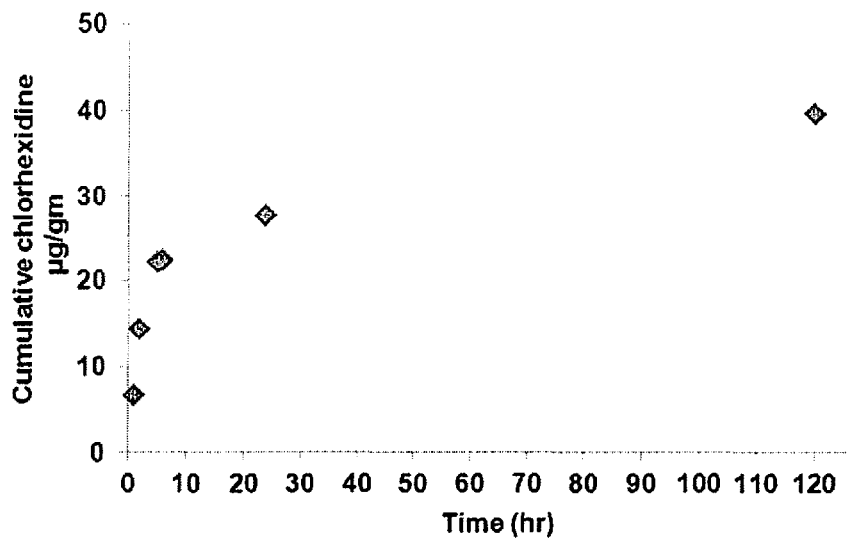
FIG. 12(a) is a graph indicating the release of chlorhexidine from the addition curable silicone adhesive of Example 21.

The cured adhesives were tested for release of antimicrobials by immersing in solutions of suitable counterions. Chlorhexidine gluconate release was performed in 50 mM phosphate buffer, and copper release was done in 0.1M sodium nitrate solution. No copper ions were observed in the aliquots, whereas a sustained release of chlorhexidine digluconate was observed (FIG. 12(a)).

Figure 12B:
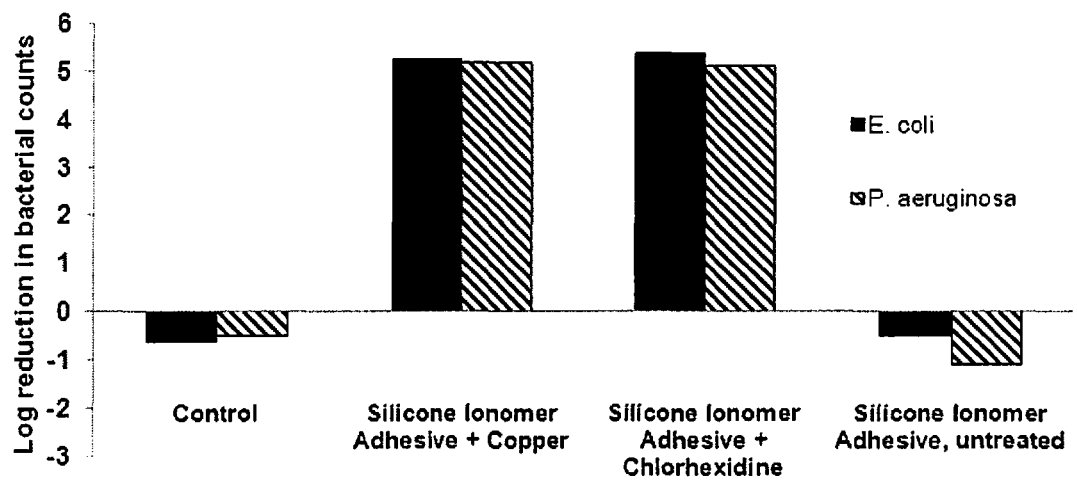
FIG. 12(b) is a graph illustrating the antimicrobial activity of addition curable silicone adhesive of Example 21.

The adhesive formulation was evaluated for antimicrobial activity using AATCC 100, as described above. *E. coli* and *P. aeruginosa* were used as representative Gram negative and Gram positive bacterial organisms. Addition cure adhesives prepared using PDMS and untreated silicone ionomer were used as controls. Both the chlorhexidine gluconate and copper containing adhesives demonstrated antibacterial activity with more than 5-log reduction in bacterial counts over 24 h (FIG. 12(b)).

Example 22

Preparation of Antimicrobial Addition Curable Silicone Adhesive from Ionic Silicone Masterbatch of Biguanide A sulfonated silicone masterbatch was prepared as described in Example 21, except that the antimicrobial was a 10% aqueous solution of pol(hexamethylene)biguanide (VANTOCIL AG, Arch Biocides). The adhesive formulation consisted of the following components:

TABLE 10

| Component | Weight (gm) |
|---|---|
| Vinyl-functional sulfonated silicone | 2.5 |
| MGT 2364 | 0.169 |
| Sulfonated silicone antimicrobial masterbatch | 2.5 |
| Vern 140 | 0.154 |
| TP 3359 | 0.383 |
| SiH/viSi ratio | 2.07 |

To this formulation, the UV-cure Platinum catalyst was added and cast on PET sheet and cured under UV radiation (105 mW/cm²) to yield a translucent adhesive film. The adhesive was subjected to C/H/N analysis to determine PHMB content, and a loading of 0.2 wt % nitrogen, corresponding to ppm of PHMB was obtained. Antimicrobial activity of the formulation using AATCC 100 and *E. coli* and *P. aeuruginosa* as test organisms revealed a 6-log reduction in bacterial counts for *E. coli* and 2.3-log reduction with *P. aeruginosa*.

Example 23

Polymer Composite Silicone Adhesive Prepared as a Free Radical Polymerized Emulsion An oil-in-water emulsion was prepared by dispersing an organic phase in an aqueous phase. The organic phase composition was as follows:

TABLE 11(a)

| Component | Wt | % |
|---|---|---|
| Acrylate functional ionic silicone | 1.6 | 10% |
| Cetyl alcohol | 0.64 | 4% |
| Lauryl acrylate | 6.88 | 43% |
| Iso-octyl acrylate | 6.88 | 43% |

The aqueous phase composition was as follows:

TABLE 11(b)

| Component | Wt | % |
|---|---|---|
| SLES (surfactant) | 4 | 11% |
| DI water | 33.5 | 89% |

The emulsion was prepared by adding 12.5 g of the organic phase into 37.5 gm of aqueous phase and blending using a high-shear homogenizer. After the emulsion was prepared, 0.031 g (0.25%) of ethylene glycol dimethyl acrylate crosslinker and 0.031 g initiator (0.25%) was added, and the mixture was heated under a nitrogen blanket at 80° C. with constant stirring. To track the polymerization, the total solid content was measured at intervals. After overnight stirring, a white emulsion was obtained. The emulsion was cast on an aluminum pan and the water was allowed to evaporate to yield a translucent, tacky adhesive film.

Tackiness of the dried adhesive was measured using the Dia-stron MTT 175 miniature tensile tester. A small amount of the emulsion was placed on the lower of the parallel-plate attachment and allowed to dry for 48 h at room temperature to a tacky film. For tack measurement, a load of 50 gm was applied to the film for a period of 30 seconds using the force arm of the instrument (35 cm² adhesive area). A peak tack value of 313.695±13.94 gmf was obtained for these test conditions.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A silicone adhesive composition comprising at least one of a polymer network, a polymer composite or a polymer emulsion wherein the network, composite or emulsion possesses covalent, non-covalent or ionic interactions and comprises a) an ionic silicone wherein the ionic silicone is a functionalized ionic silicone having the formula:

$$M^1_a M^2_b M^3_c D^1_d D^2_e D^3_f T^1_g T^2_h T^3_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1, R^2, R^3, R^5, R^6, R^8, R^9, R^{10}, R^{11}, R^{13}, R^{15}$ and $R^{16}$ are aliphatic, aromatic or fluoro containing monovalent hydrocarbon radicals containing from 1 to about 60 carbon atoms, where $R^4$, $R^{12}$ and $R^{17}$ are monovalent radical bearing ion-pairs having the formula (II):

$$-A-I^{x-} M_n^{y+} \quad (II)$$

where A is a divalent hydrocarbon or hydrocarbonoxy spacing group, the divalent hydrocarbon group being selected from the group consisting of —(CHR')$_k$C$_6$H$_4$(CH$_2$)$_l$—, —CH$_2$CH(R')(CH$_2$)$_k$C$_6$H$_4$—, —CH$_2$CH(R')(CH$_2$)$_l$C$_6$H$_3$R"— and
—CH$_2$CH(R')(CH$_2$)$_l$C$_6$H$_2$R$^1$R"— where R' is a hydrogen or defined by R$^1$, R" is a monovalent radical specifically from about 1 to about 20 carbon atoms, sulfur atom(s), nitrogen atom(s), oxygen atom(s) or a radical containing combinations of the above atoms, where l has a value of 0 to 20, and k has a value of 0 to 20, where I is an ionic group selected from sulfonate —SO$_3^-$, sulfate —OSO$_3^-$, carboxylate —COO$^-$, phosphonate —PO$_3^{2-}$ and phosphate —OPO$_3^{2-}$, where M is hydrogen or a cation independently selected from alkali metals, alkali earth metals, transition metals, metal complexes, quaternary ammonium and phosphonium groups, organic cations, alkyl cations, cationic hydrocarbons and cationic polymers; or, zwitterions having the formula (III):

$$—R'—NR''_2{}^+—R'''—I \quad (III)$$

where R' is a divalent hydrocarbon radical containing from 1 to about 20 carbon atoms, where R" is a monovalent hydrocarbon radical containing from 1 to about 20 carbon atoms, where R'" is a divalent hydrocarbon radical containing from 2 to about 20 carbon atoms, where I is an ionic group selected from sulfonate —SO$_3^-$, sulfate —OSO$_3^-$, carboxylate —COO$^-$, phosphonate —PO$_3^{2-}$ and phosphate —OPO$_3^{2-}$, where R$^7$, R$^{14}$ and R$^{18}$ are independently selected from hydrogen or monovalent hydrocarbon radicals selected from —OR$^{20}$, unsaturated monovalent radicals, monovalent epoxy group-containing radicals, monovalent sulfur atom-containing radicals, monovalent organosilane groups and monovalent hydroxyl group containing radicals, and a monovalent hydrocarbon group containing one or more of a halogen moiety, a carboxylate moiety, an imine moiety, an isocyanate moiety, an amide moiety, a nitrile moiety, or a tertiary amine moiety containing other than alkyl groups moiety, where R$^{20}$ is hydrogen or a monovalent hydrocarbon radical containing from 2 to about 60 carbon atoms, where superscripts x and y are independently selected from 1 to 6, and x is a multiple of n and y, and where the subscripts a, b, c, d, e, f, g, h, I and j are zero or positive and subject to the following limitations: the sum a+b+c+d+e+f+g+h+i+j is greater than or equal to 2 and less than or equal to 6000, d+e is greater than zero, and b+e+h is greater than zero;

b) at least one member selected from the group consisting of monomer, oligomer, silicone polymer free from any ionic groups and prepolymer; and, c) a catalyst or a reaction initiator.

2. The silicone adhesive composition of claim 1 wherein the monovalent hydrocarbon radical is independently selected from the group consisting of methyl, ethyl, n-propyl, iso-propyl, n-butyl, isobutyl, tert-butyl, n-pentyl, iso-pentyl, neopentyl, tert-pentyl, hexyl, heptyl, octyl, isooctyl, 2,2,4-trimethylpentyl, nonyl, decyl, cycloalkyl radicals and aryl radicals groups.

3. The silicone adhesive composition of claim 2, wherein the cycloalkyl radicals are independently selected from the group consisting of cyclopentyl, cyclohexyl, cycloheptyl and methylcyclohexyl radicals.

4. The silicone adhesive composition of claim 2 wherein the aryl radicals are independently selected from the group consisting of phenyl, naphthyl; o-, m- and p-tolyl, xylyl, ethylphenyl, and benzyl.

5. The silicone adhesive composition of claim 1 wherein the divalent hydrocarbon group is an alkylene group of the formula —(CHR$^{19}$)$_m$— where m has a value of 1 to about 20 and R$^{19}$ is hydrogen or R$^1$.

6. The silicone adhesive composition of claim 1 wherein the divalent hydrocarbonoxy group is selected from the group consisting of —(CHR$^{19}$)$_m$—(O—CHR$^{19}$CH$_2$)$_{m'}$—O—(CH$_2$)$_l$ where R$^{19}$ is hydrogen or R$^1$, l has a value of from 1 to 20, m has a value from 0 to 20 and m' has a value from 0 to 50.

7. The silicone adhesive composition of claim 1 wherein each of R$^7$, R$^{14}$ and R$^{18}$ are a monovalent hydrocarbon radical selected from the group of the formulae (IV) to (XIV)

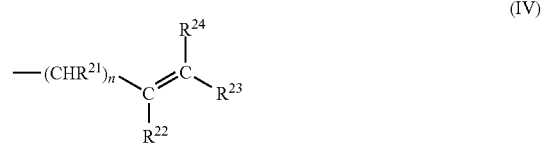

(IV)

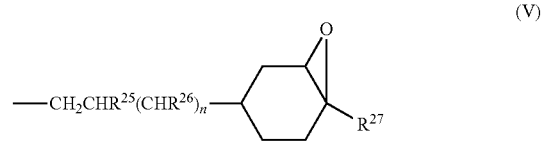

(V)

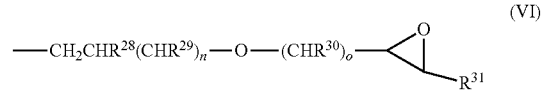

(VI)

-continued

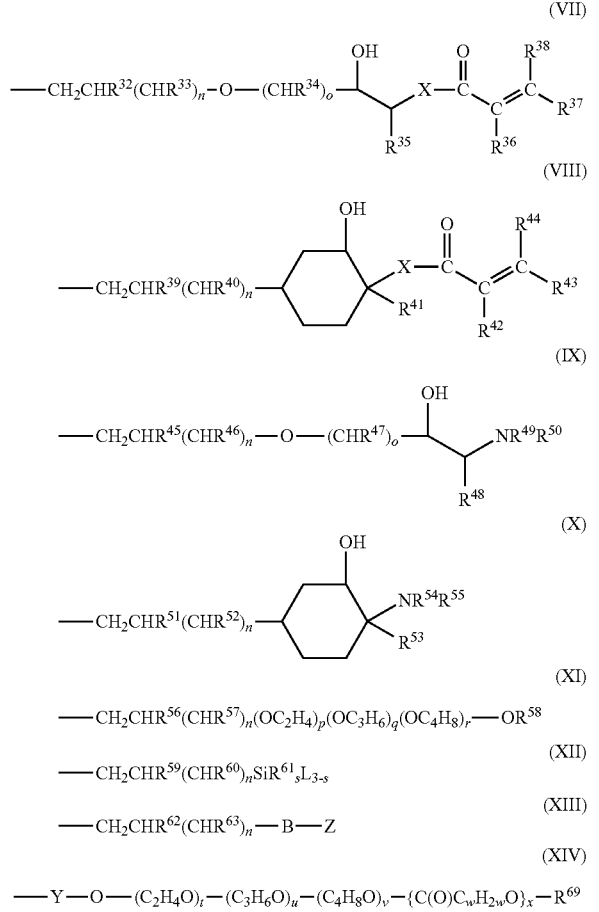

—CH$_2$CHR$^{59}$(CHR$^{60}$)$_n$SiR$^{61}$$_s$L$_{3-s}$ (XII)

—CH$_2$CHR$^{62}$(CHR$^{63}$)$_n$—B—Z (XIII)

—Y—O—(C$_2$H$_4$O)$_t$—(C$_3$H$_6$O)$_u$—(C$_4$H$_8$O)$_v$—{C(O)C$_w$H$_{2w}$O}$_x$—R$^{69}$ (XIV)

where R$^{21}$, R$^{26}$, R$^{29}$, R$^{30}$, R$^{33}$, R$^{34}$, R$^{40}$, R$^{46}$, R$^{47}$, R$^{52}$ and R$^{63}$ are independently selected from hydrogen, —OH, —R$^{66}$ and aliphatic/aromatic monovalent hydrocarbon having from 1 to 60 carbon atoms, where R$^{22}$, R$^{23}$, R$^{24}$, R, R$^{27}$, R$^{28}$, R$^{31}$, R$^{32}$, R$^{35}$, R$^{36}$, R$^{37}$, R$^{38}$, R$^{39}$, R$^{41}$, R$^{42}$, R$^{43}$, R$^{44}$, R$^{45}$, R$^{48}$, R$^{51}$, R$^{53}$, R$^{56}$, R$^{57}$, R$^{59}$, R$^{60}$, R$^{61}$ and R$^{62}$ are independently selected from hydrogen, aliphatic/aromatic monovalent hydrocarbon having from 1 to 60 carbon atoms, where R$^{58}$ is aliphatic/aromatic monovalent hydrocarbon having from 2 to 60 carbon atoms, where R$^{49}$, R$^{50}$, R$^{54}$ and R$^{55}$ are independently selected from hydrogen, —C$_t$H$_{2t}$OH and aliphatic/aromatic monovalent hydrocarbon having from 1 to 60 carbon atoms, wherein t is a positive integer, where L is a monovalent radical independently selected from halogen, OR$^{64}$, —CO(O)R$^{65}$, —N═CR$^{66}$$_2$, —NCO, —NC(O)R$^{67}$, —C≡N, —N═N and —NR$^{68}$$_2$ where R$^{64}$, R$^{65}$, R$^{66}$, R$^{67}$ and R$^{68}$ are independently selected from the group consisting of hydrogen and alkyl, alkenyl, cycloalkyl and aryl containing from 1 to 60 carbon atoms, where Z is a monovalent radical independently selected from halogen, OR$^{64A}$, —CO(O)R$^{65}$, —N═CR$^{66}$$_2$, —NCO, —NC(O)R$^{67}$, —C≡N, —N—N and —NR$^{68A}$2 where R$^{65}$, R$^{66}$ and R$^{67}$ are independently selected from the group consisting of hydrogen and alkyl, alkenyl, cycloalkyl and aryl containing from 1 to 60 carbon atoms, and R$^{64A}$ is selected from the group consisting of alkyl, alkenyl, cycloalkyl and aryl containing from 2 to 60 carbon atoms, and where R$^{68A}$ is selected from the group consisting of alkenyl, cycloalkyl and aryl containing from 2 to 60 carbon atoms, where X is divalent radical selected from —O—, —N— and —S— linkages, where Y and B are divalent radicals selected from a linear, branched, cyclic hydrocarbon radical or aralkyl radical containing from 1 to 60 carbon atoms, where R$^{69}$ is a hydrogen or monovalent alkyl radical with 1 to 20 carbon atoms or an acyl group, where the subscript n is zero or positive integer and has a value in the range of 0 to 60, where subscript o is positive integer and has a value in the range of 1 to 60, where subscripts p, q and r are zero or positive and independently selected from a value in the range of 0 to 100, subject to the limitation of p+q+r being greater than or equal to i, where s is zero or a positive integer and has a value of 0 to 2, where t, u, v and x are zero or positive integers and subject to the limitation t+u+v+x is greater than or equal to 1, and where w is a positive integer.

8. The silicone adhesive composition of claim 1 wherein the subscripts a, b, d, e, g and h are subject to the limitations a+b≥2, d+e≥0, g+h≥0 and b+e+h>0.

9. The silicone adhesive composition of claim 1, including a silicone compound having the formula:

A'$_{a'}$A"$_{b'}$(OH)$_{c'}$SiO$_{(4-a'-b'-c')/2}$ (XV)

where A' is an alkenyl group bonded directly to the silicon atom, A" is a group selected from un-substituted or substituted monovalent hydrocarbyl, epoxy or alkoxy, but excluding alkenyl, and a', b' and c' are zero or positive numbers with the proviso that a'+b'+c' is greater than 0.

10. The silicone adhesive composition of claim 9 wherein A' is vinyl, allyl, butenyl, hexenyl or decenyl.

11. The silicone adhesive composition of claim 9 wherein A" is directly bonded to the silicon atom and is selected from unsubstituted or substituted monovalent hydrocarbyl, excluding alkenyl, and alkoxy, wherein the hydrocarbyl group is selected from the group consisting of methyl, ethyl, n-propyl, iso-propyl, n-butyl, isobutyl, tert-butyl, n-pentyl, iso-pentyl, neopentyl and tert-pentyl; hexyl, heptyl, octyl, nonyl, decyl, cyclopentyl, cyclohexyl and cycloheptyl, methylcyclohexyl radicals, phenyl, naphthyl; o-, m- and p-tolyl, xylyl, ethylphenyl, benzyl, 3-chloropropyl, 3,3,3-trifluoropropyl, 2-(nonafluorobutyl)ethyl, ethylbenzyl, 1-phenethyl methoxy, ethoxy, n-propoxy, and i-propoxy, and wherein the OH is directly bonded to the silicon.

12. The silicone adhesive composition of claim 1, including the organohydrogen functional silicone compound of the formula:

wherein A* is directly bonded to the silicon atom and is selected from the group consisting of methyl, ethyl, n-propyl, iso-propyl, n-butyl, isobutyl, tert-butyl, n-pentyl, iso-pentyl, neopentyl and tert-pentyl; hexyl; heptyl; n-octyl, isooctyl, 2,2,4-trimethylpentyl group, nonyl, decyl, cyclopentyl, cyclohexyl and cycloheptyl, methylcyclohexyl radicals, phenyl, naphthyl; o-, m- and p-tolyl, xylyl, ethylphenyl, benzyl, 3-chloropropyl, 3,3, 3-trifluoropropyl, 2-(nonafluorobutyl)ethyl, and ethylbenzyl, where d' is a positive number, and e' is 0 or a positive number.

13. The silicone adhesive composition of claim 1 wherein the adhesive is in form of a polymer composite.

14. The silicone adhesive composition of claim 13 wherein the composition further comprises one or more polymerizable monomer(s) or prepolymer(s) or polymer(s) or combinations thereof.

15. The silicone adhesive composition of claim 13 wherein the polymer composite is obtained via polymerization of the silicone ionomer in presence of the polymer(s).

16. The silicone adhesive composition of claim 13 wherein the polymer composite is obtained via simultaneous or sequential polymerization of the silicone ionomer and the monomer(s) or prepolymer(s) or their mixtures.

17. The silicone adhesive composition of claim 13 wherein the polymer composite is obtained by physical or reactive blending of the silicone ionomer with suitable polymers.

18. The silicone adhesive composition of claim 14 wherein the monomers and prepolymers are selected from one or more of free-radical polymerization effective monomers or prepolymers.

19. The silicone adhesive compositions of claim 18 wherein the monomers and prepolymer comprise of at least one free-radical polymerization effective group selected from methacrylate, butylacrylate, propylacrylate, N,N-dimethylacrylamide, methacrylic acid, N-isopropyl acrylamide, 2-hydroxy-ethyl-methacrylate (HEMA) and methacrylic acid, 3-[tris(trimethylsiloxy)silyl]propyl methacrylate, acrylate and methacrylate functional carbosilane molecules, hexafunctional urethane acrylates, dipentaerythritol pentaacrylate, ethoxylated pentaerythritol tetraacrylate, di-trimethylolpropane tetraacrylate, pentaerythritol triacrylate, trimethylolpropane triacrylate, ethoxylated trimethylolpropane triacrylate, butanediol diacrylate, tripropylene glycol diacrylate, trimethylolpropane trimethacrylate, oligofunctional urethane acrylates, tetraacrylate monomer, polyester acrylate oligomers, and combinations thereof.

20. The silicone adhesive composition of claim 14, wherein the monomers or prepolymers are selected from two or more addition polymerizable compounds.

21. The silicone adhesive composition of claim 20 wherein the monomer or prepolymers comprise compounds selected from hydride functional silicones, olefenically unsaturated organic moieties or organomodified silicones, compounds selected from epoxy, amino, hydroxyl or carboxyl moieties, compounds selected from isocyanates, hydroxyls or amine.

22. The silicone adhesive composition of claim 14 wherein the monomers or prepolymers are selected from one or more condensation curable compounds.

23. The silicone adhesive composition of claim 22 wherein the monomer or prepolymer comprises of two or more condensation polymerisable moieties selected from silanol, alkoxy silanes, silicates, silicic acids, and acyloxy silanes.

24. The silicone adhesive composition of claim 22 wherein the monomer or prepolymer comprises of the compounds forming poly esters, polyamides, polyimides, polyanhydrides, polysulfones, polycarbonates and polyetheretherketones.

25. The silicone adhesive composition of claim 22 wherein the monomer or prepolymer comprises two or more condensation polymerisable moieties selected from silanol, alkoxy silanes, silicates, silicic acids, acyloxy silanes and one or more of compounds forming polyesters, polyamides, polyimides, polyanhydrides, polysulfones, polycarbonates and polyetheretherketones.

26. The silicone adhesive composition of claim 14 wherein the monomer or prepolymer comprise of one or more ring opening polymerisable moieties selected from lactides or glycolides.

27. The silicone adhesive composition of claim 14 comprising at least one of the polymers selected from sulfonated polystyrene, polyelectrolytes, sulfonated polyesters, polyacrylates, polyacrylamides, polyurethanes, polyethers, polyesters, polylactones, polylactides, polyglycolides, polyacids, polyamides, polyamines, polyethylene, polypropylene, poly (alkylene oxides) selected from polyethylene oxide, polypropylene oxide, polybutadiene, polybutylene, polyacrylonitrile, polyvinyl chloride, polyvinyl acetate, polystyrene, polysulfone, PEEK, polycarbonate, polyepoxides, fluoropolymers selected from PTFE, polyvinylenedifluoride, synthetic and natural rubber, phenol formaldehyde, melamine formaldehyde, urea formaldehyde, polymers of natural or semi-synthetic origin selected from polysaccharides, cellulose, proteins, polypeptides, poly(amino acids), organosilicon polymers selected from polysiloxanes, polysilicates, polysilsesquioxanes, polysilanes, ionically modified versions of the above, and isomers and co-polymers of the above polymers.

28. The silicone adhesive composition of claim 14 wherein the silicone ionomer and the polymer interact with each other.

29. The silicone adhesive composition of claim 28 wherein the silicone ionomer and the polymer interact via ionic interactions between similar or dissimilar ionic groups.

30. The silicone adhesive composition of claim 29 wherein the interaction is via hydrophobic interactions, crystalline phases, acid-base interactions, co-ordination complexes, π-interactions or hydrogen bonding.

31. The silicone adhesive composition of claim 13 wherein the silicone ionomer and the polymer are covalently linked through condensation reactions via multiple functional groups in their structures, and involving the liberation of small molecules.

32. The silicone adhesive composition of claim 1 further comprising a catalyst.

33. The silicone adhesive composition of claim 32 wherein the catalyst is a condensation catalyst selected from dibutyl tin dilaurate, tin octanoate and other alkyltin compounds; acid-base salts of other metals selected from titanium, iron, zinc, aluminum, and organic ammonium compounds and silanolate salts.

34. The silicone adhesive composition of claim 32 wherein the catalyst is a transition metal based catalyst and selected from platinic chloride, chloroplatinic acid, bis(acetylacetonato)platinum, ($\eta^5$-cyclopentadienyl)trialkylplatinum complexes, Pt triazenido complex, $Pt(PPh_3)_2Cl_2$, iron, palladium and rhodium complexes.

35. The silicone adhesive composition of claim 1 further comprising an initiator.

36. The silicone adhesive composition of claim 35 wherein the initiator is a thermal or photoinitiator and is selected from benzoin, benzoin methyl ether, benzoin ethyl ether, benzoin propyl ether, benzoin-n-butyl ether, benzoin isobutyl ether, acetoin, butyroin, toluoin, benzil, benzophenone, para methoxybenzophenone, 2,2-diethoxyacetophenone, alpha-alpha-dimethoxy-alpha-phenylacetophenone, methylphenyl glyoxylate, ethyphenyl glyoxylate, 4,4'-bis-(dimethylaminobenzophenone), propiophenone, acetophenone, 1-hydroxycyclohexyl phenyl ketone, 2,2-diethoxyacetophenone, ethlphenylpyloxylate, phenanthraquinone, and 2-hydroxy-2-methyl-1-phenyl-propan-1-one, tetramethylthiuram monosulfide, tetramethylthiuram disulfide, azobisisobutyronitrile, azobis-2,4-dimethylvaleronitrile, benzoyl peroxide, di-tert-butyl peroxide, 7-chlorothioxanthone, 2,4-diethylthioxanthone, 2,4-diisopropylthioxanthone, acylophosphine oxide photoinitiators and combinations thereof.

37. The silicone adhesive composition of claim 35 wherein the initiator is a cationic photoinitiator and is selected from the group consisting of diaryliodonium salts, triarylsulfonium salts, triarylselenonium salts, tetraarylphosphonium salts and aryldiazonium salts, respectively represented by the formulas $R^{29}_2I^+Y^-$, $R^{29}_3S^+Y^-$, $R^{29}_3Se^+Y^-$, $R^{29}_4P^+Y^-$ and $R^{29}N_4^+Y^-$, wherein, $R^{29}$ represents an aryl group, and $Y^-$ represents an anion selected from $SbF_6^-$, $AsF_6^-$, $PF_6^-$, $BF_4^-$, $HSO_4^-$ and $ClO_4^-$.

38. The silicone adhesive composition of claim 1 further including one or more functional additives selected from fillers, solvents, surfactants, pigments, colorants, mold release agents, adhesion promoters, plasticizers, tackifiers, excipients, UV absorbers, photosensitizers, flattening agents, crosslinkers, chain terminators, rheology modifiers, thickeners, foam suppressers, antioxidants, drugs, fillers, bioactives, exfoliants, enzymes, proteins and peptides, medicinal compounds, biocides, oral care agents, oxidizing agents, reducing agents, skin protectants, essential oils, insect repellents, UV light absorbing agents, solar filters, pigments, hydrating agents, vitamins and their combinations thereof.

39. The silicone adhesive composition of claim 38 wherein the fillers are selected from re-enforcing or non-reinforcing fillers, conductive or non-conductive fillers, and are selected from selected from particulate forms of oxides of titanium, cerium, aluminum, zirconium and other metals and metalloids, metal or metal oxide nanoparticles with and without surface modification, carbon black, carbon nanotubes, graphite, graphene, glass fibers, talc, carborundum, mica, boron nitride, clay, inorganic fillers, polysaccharides, natural and synthetic fibers, and suitable combinations thereof.

40. A hydrophilic, moisture permeable woundcare article comprising the silicone adhesive composition of claim 1.

41. The woundcare article of claim 40 comprising antimicrobial agents selected from silver, copper, chlorhexidine, biguanide, zinc, benzalkonium chloride, polyquaternary ammonium compounds, chitosan and its derivatives, antimicrobial peptides selected from nisin, pediocin, and pleuricidin and their derivatives and recombinant forms and possessing antimicrobial property.

42. A transdermal drug delivery article comprising the silicone adhesive composition of claim 1 comprising at least one drug.

43. The transdermal drug delivery article of claim 42 wherein the drugs are selected from drugs that act upon the central nervous system selected from clozapine, risperidone, chordiazepoxide, buspirone, desipramine, maprotiline, timolol, selegiline; drugs affecting renal and cardiovascular function selected from acetazolamide, isosorbide, furosemide, chlorothiazide, amiloride, captopril, enalapril, lisinopril, nifedipine, verapamil, lidocaine, propranolol, amiodarone, pravastatin, probucol, oxycontin; drugs affecting gastrointestinal function selected from cimetidine, omeprazole and ranitidine; drugs for treatment of helminthiasis selected from thiabendazole and mebendazole; drugs for the treatment of microbial diseases selected from trimethoprim, norfloxacin, ciprofloxacin, penicillin, kanamycin, fluconazole, acyclovir, ritonavir, and ganciclovir; drugs for the treatment of neoplastic diseases selected from dacarbazine, busulfan, and triazenes; drugs for treatment of nutrient deficiency selected from folic acid, niacinamide, ascorbic acid and thiamine; drugs for hormonal replacement therapy selected from testosterone and other androgenic steroids, progestational drugs, estradiol and their analogues and norethindrone; drugs for inhibition of adrenocortical hormones selected from cortisol, cortisone and prednisone; drugs used in dermatology selected from betamethasone, dipropionate, hydrocortisone, dexamethasone sodium phosphate, retinal, tretinoin, isotretinoin, dapsone, calipotriene, ketoconazole, clotrimazole itraconazole and arotinoid; anti-inflammatory agents selected from ibuprofen, ketoprofen, diclofenac; anti-histamines selected from azelastine, hydroxyzine, desloratadine, carbinoxamine, fexofenadine and brompheniramine; respiratory agents selected from tadalafil, laronidase, ciclesonide and indacaterol maleate; sympathomimetics selected from catecholamines, epinephrine and dopamine; miotics; cholinergic agonists selected from alvameline, muscarine, nicotine and pilocarpine; humoral agents; anti-spasmodics selected from baclofen, tizanidine and dantrolene; anti-depressant drugs; anti-diabetic drugs; anti-anorectic drugs; tranquilizers; antipsychotics selected from olanzapine, risperidone, quetiapine, ziprasidone and amisulpride; anti-pyretics selected from paracetamol, nabumetone; drugs for Parkinson's disease, anti-malarials, anti-ulcerative agents, therapeutic agents and combinations thereof.

44. The transdermal drug delivery article of claim 42 comprising an excipient wherein the excipient is selected from sugars and sugar derivatives selected from acacia, dextrin, dextrose, fructose, lactose, maltodextrin, mannitol, sorbitol, sucrose and xylitol; starch and derivatives; cellulosic materials selected from sodium carboxymethylcellulose, microcrystalline cellulose, cellulose acetate phthalate, sodium croscarmellose, methyl cellulose, ethyl cellulose, HPMC, hydroxypropyl cellulose; polysaccharides selected from xanthan gum, guar gum; polyethers selected from poloxamers, and polyoxyalkylene ethers; polyvinyl alcohols and acetates; acrylic acid and methacrylic acid polymers selected from Carbopol, Carbomer, Covacryl, polacrilin potassium; pyrrolidone derivatives selected from povidone, crosspovidone and Kollidon; glycouran polymers selected from hyaluronic acid, alginic acid, alginate, agar; and other excipients selected from cholesterol, lecithin, gelatin and mallic acid.

45. The silicone adhesive composition of claim 1, wherein c+f+i is greater than zero.

46. The silicone adhesive composition of claim 1, wherein when I is carboxylate COO—, c+f+i is greater than zero.

* * * * *